(12) United States Patent
Wiessler et al.

(10) Patent No.: US 9,169,283 B2
(45) Date of Patent: Oct. 27, 2015

(54) POST-SYNTHETIC MODIFICATION OF NUCLEIC ACIDS BY INVERSE DIELS-ALDER REACTION

(75) Inventors: Manfred Wiessler, Frankenthal (DE); Peter Lorenz, Dossenheim (DE); Heinz Fleischhacker, Dossenheim (DE); Karola Ursula Fleischhacker, legal representative, Dossenheim (DE); Marlen Fleischhacker, legal representative, Butzbach (DE); Nadja Fleischhacker, legal representative, Dossenheim (DE); Christian Kliem, Heppenheim (DE); Andres Jäschke, Heidelberg (DE); Juliane Schoch, Heidelberg (DE)

(73) Assignees: DEUTSCHES KREBSFORSCHUNGSZENTRUM, Heidelberg (DE); RUPRECHT-KARLS-UNIVERSITAET HEIDELBERG, Heidelberg (DE)

( * ) Notice: Subject to any disclaimer, the term of this patent is extended or adjusted under 35 U.S.C. 154(b) by 159 days.

(21) Appl. No.: 13/557,698

(22) Filed: Jul. 25, 2012

(65) Prior Publication Data

US 2013/0085271 A1    Apr. 4, 2013

Related U.S. Application Data

(63) Continuation of application No. PCT/EP2011/000491, filed on Feb. 3, 2011.

(30) Foreign Application Priority Data

Feb. 3, 2010    (EP) .................................... 10001122

(51) Int. Cl.
   *C07H 21/04*    (2006.01)
   *C07H 21/00*    (2006.01)
   *C07H 1/00*     (2006.01)

(52) U.S. Cl.
   CPC .................. *C07H 1/00* (2013.01); *C07H 21/00* (2013.01); *C07H 21/04* (2013.01)

(58) Field of Classification Search
   CPC ................................ C07H 21/00; C07H 21/04
   See application file for complete search history.

(56) References Cited

U.S. PATENT DOCUMENTS

2010/0016545 A1*    1/2010    Wiessler et al. ............... 530/300

FOREIGN PATENT DOCUMENTS

| EP | 1 867 638 A1 | 12/2007 |
| WO | WO 02/16378 A1 | 2/2002 |

OTHER PUBLICATIONS

Definition of small interfering RNA, Dorland's Illustrated Medical Dictionary, http://search.credoreference.com/content/entry/ehsdorland/small_interfering_rna/0, accessed online on Jun. 11, 2014.*
Blackman et al., J. Am. Chem. Soc., 2008, 130, p. 13518-13519.*
Borsenberger et al., Nucleic Acids Res., 2009, 37(5), p. 1477-1485.*
Gutsmiedl et al., Org. Lett., 2009, 11(11), p. 2405-2408.*
International Search Report and Written Opinion of PCT Application No. PCT/EP2011/000491 with a mailing date of Aug. 2, 2011.
Hill et al.; "Diels—Alder Bioconjugation of Diene-Modified Oligonucleotides"; Journal of Organic Chemistry; vol. 66, No. 16, pp. 5352-5358 (Jul. 12, 2001).

* cited by examiner

*Primary Examiner* — Jonathan S Lau
(74) *Attorney, Agent, or Firm* — Perkins Coie LLP; Viola T. Kung

(57) ABSTRACT

The present invention concerns a method and a kit for the post-synthetic modification of nucleic acids via an inverse Diels-Alder reaction.

13 Claims, 11 Drawing Sheets

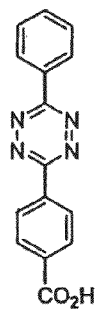 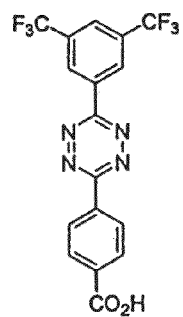
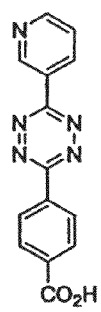 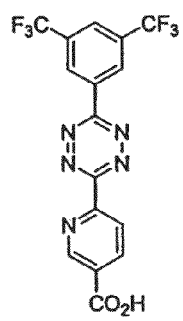 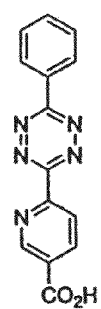
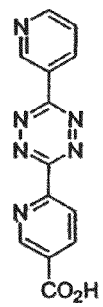 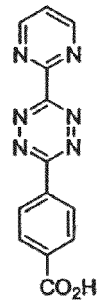
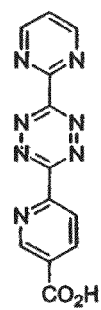 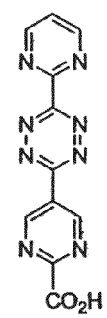
Fig. 2

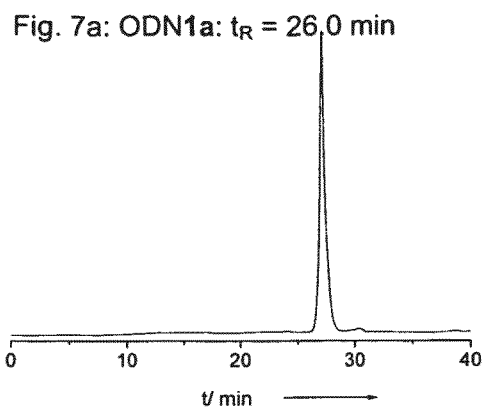
Fig. 7a: ODN1a: $t_R$ = 26.0 min
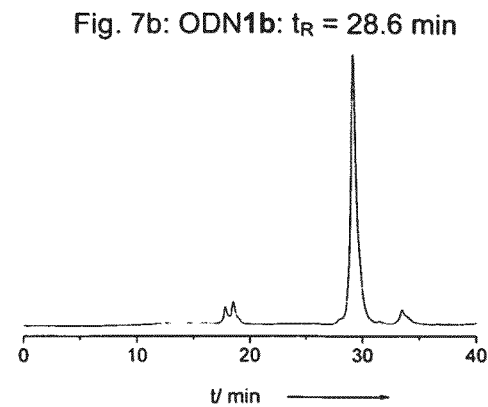
Fig. 7b: ODN1b: $t_R$ = 28.6 min
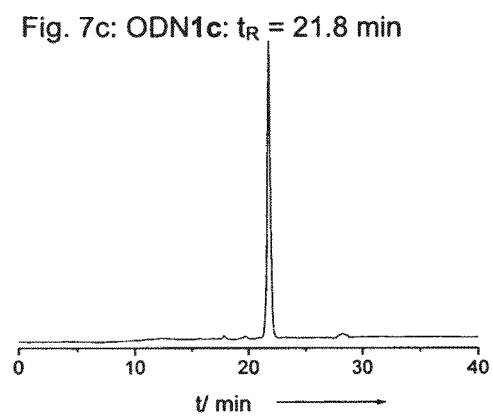
Fig. 7c: ODN1c: $t_R$ = 21.8 min
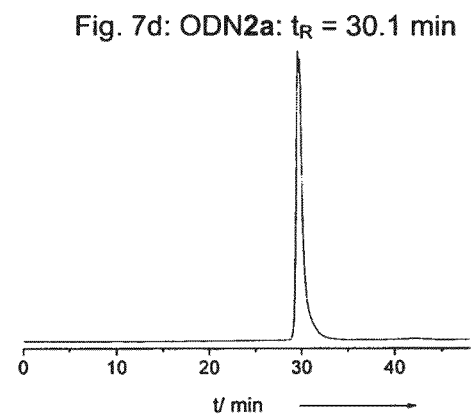
Fig. 7d: ODN2a: $t_R$ = 30.1 min
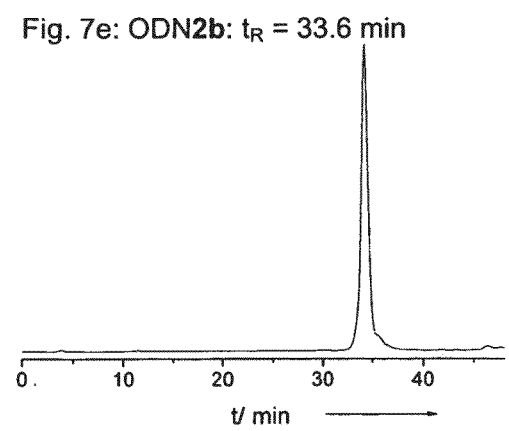
Fig. 7e: ODN2b: $t_R$ = 33.6 min
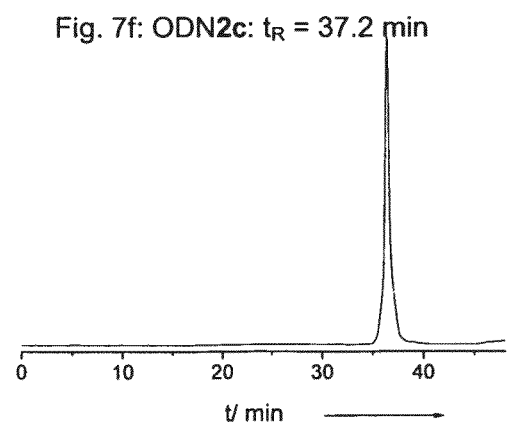
Fig. 7f: ODN2c: $t_R$ = 37.2 min

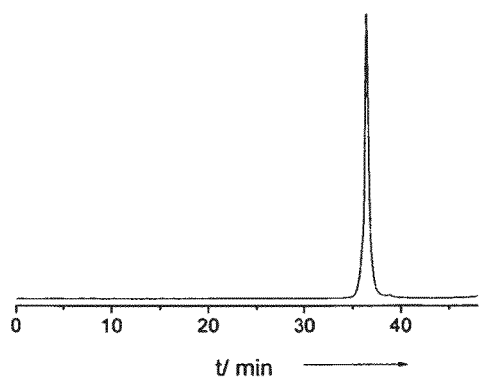
Fig. 7g: ODN2d: $t_R$ = 37.2 min
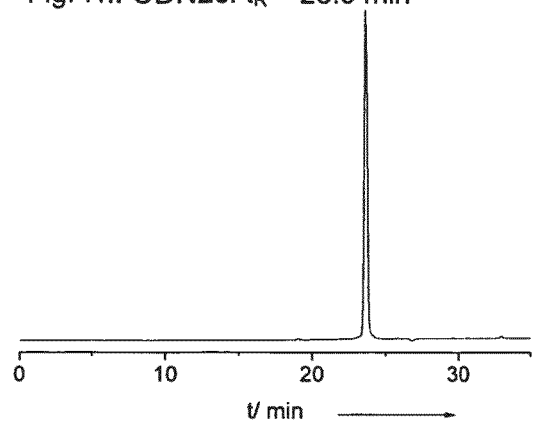
Fig. 7h: ODN2e: $t_R$ = 23.6 min
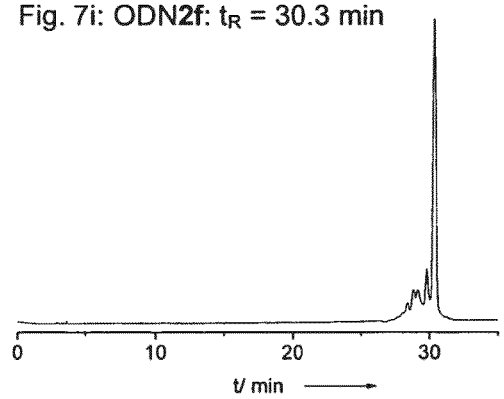
Fig. 7i: ODN2f: $t_R$ = 30.3 min ODN1a/5: $t_R$ (DA product) = 20.8-26.5 min ODN2c/5: $t_R$ (DA product) = 27.4-34.4 min Negative control: unmodified hexamer/5 (1eq, 24 h)

Negative control: ODN3a/5 (10eq, 60 h)

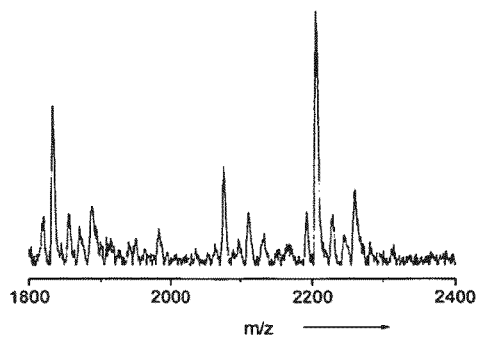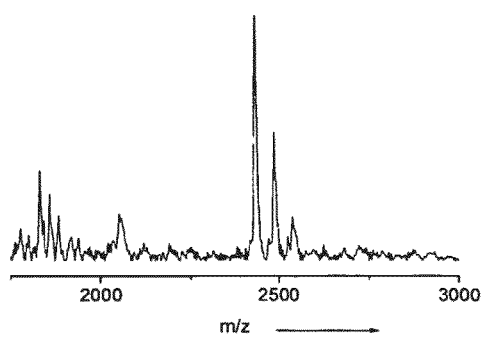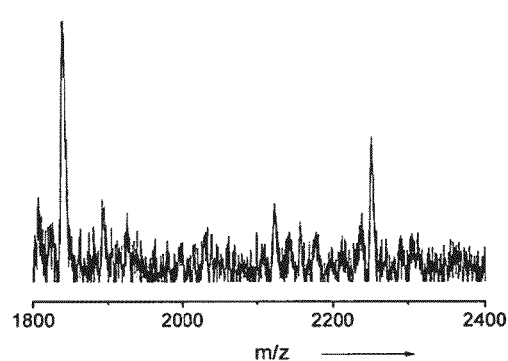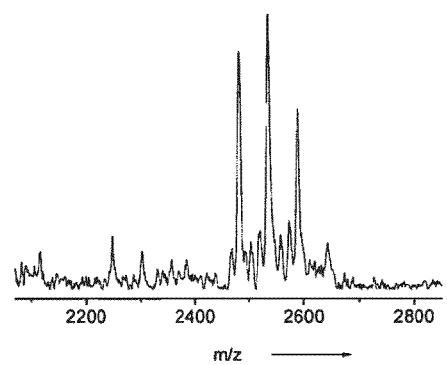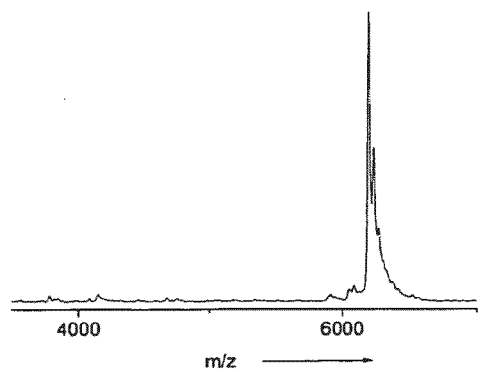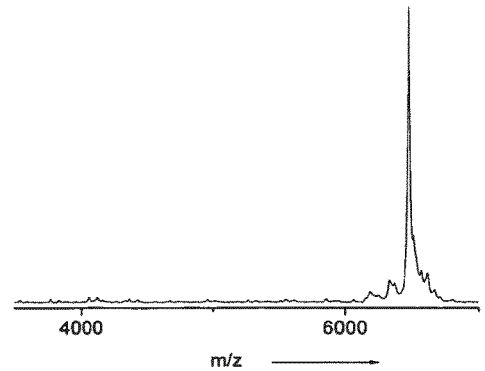
Fig.9

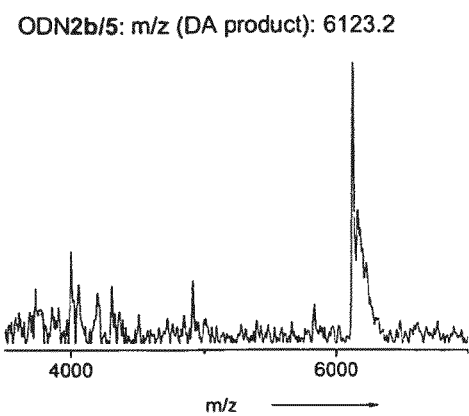
ODN2b/5: m/z (DA product): 6123.2
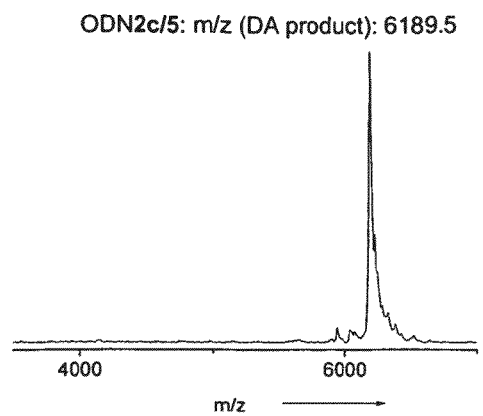
ODN2c/5: m/z (DA product): 6189.5
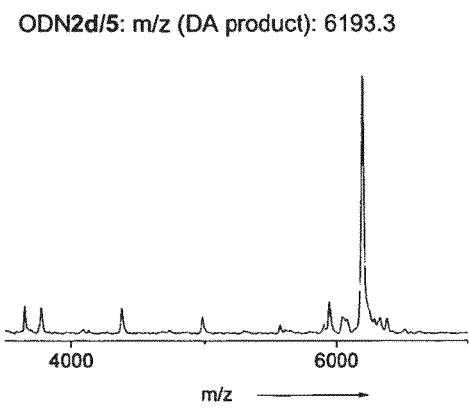
ODN2d/5: m/z (DA product): 6193.3
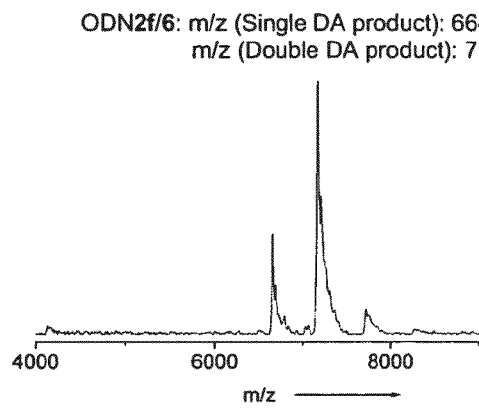
ODN2f/6: m/z (Single DA product): 6648.8;
m/z (Double DA product): 7174.0
Fig. 9 (Cont.)

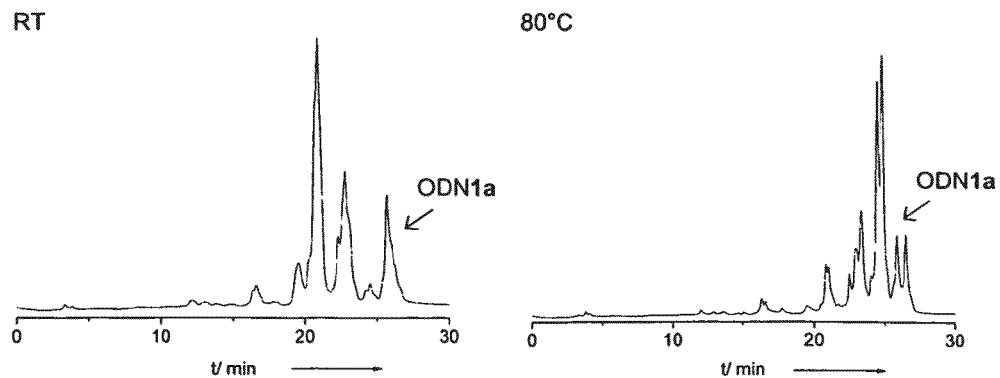
Fig. 10
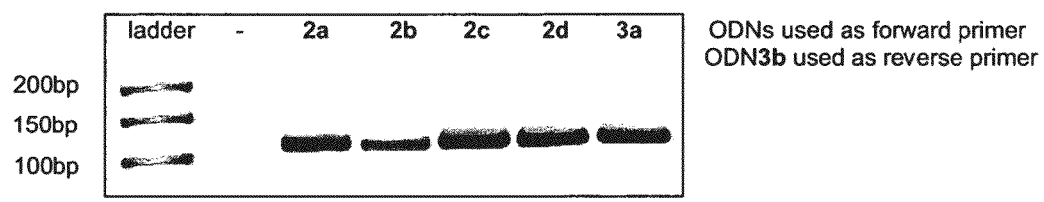
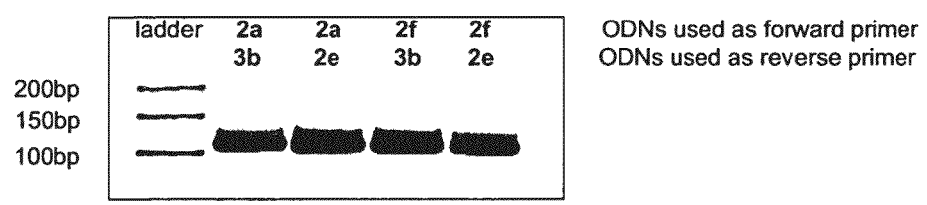
Fig. 11

SEQUENCE LISTING

<160> NUMBER OF SEQ ID NOS: 19

<210> SEQ ID NO 1
<211> LENGTH: 7
<212> TYPE: DNA
<213> ORGANISM: artificial sequence
<220> FEATURE:
<223> OTHER INFORMATION: oligonucleotide ODN1a
<220> FEATURE:
<221> NAME/KEY: misc_feature
<222> LOCATION: (1)..(1)
<223> OTHER INFORMATION: n is a, c, g, or t

<400> SEQUENCE: 1 ntgctca                                                                7

<210> SEQ ID NO 2
<211> LENGTH: 7
<212> TYPE: DNA
<213> ORGANISM: artificial sequence
<220> FEATURE:
<223> OTHER INFORMATION: oligonucleotide ODN1b
<220> FEATURE:
<221> NAME/KEY: misc_feature
<222> LOCATION: (4)..(4)
<223> OTHER INFORMATION: n is a, c, g, or t

<400> SEQUENCE: 2 tgcntca                                                                7

<210> SEQ ID NO 3
<211> LENGTH: 7
<212> TYPE: DNA
<213> ORGANISM: artificial sequence
<220> FEATURE:
<223> OTHER INFORMATION: oligonucleotide ODN1c
<220> FEATURE:
<221> NAME/KEY: misc_feature
<222> LOCATION: (7)..(7)
<223> OTHER INFORMATION: n is a, c, g, or t

<400> SEQUENCE: 3 tgctcan                                                                7

<210> SEQ ID NO 4
<211> LENGTH: 20
<212> TYPE: DNA
<213> ORGANISM: artificial sequence
<220> FEATURE:
<223> OTHER INFORMATION: oligonucleotide ODN2a
<220> FEATURE:
<221> NAME/KEY: misc_feature
<222> LOCATION: (1)..(1)
<223> OTHER INFORMATION: n is a, c, g, or t

<400> SEQUENCE: 4
nggagctcag ccttcactgc                                                 20

<210> SEQ ID NO 5
<211> LENGTH: 19
<212> TYPE: DNA
<213> ORGANISM: artificial sequence
<220> FEATURE:
<223> OTHER INFORMATION: oligonucleotide ODN2b
<220> FEATURE:
<221> NAME/KEY: misc_feature
<222> LOCATION: (6)..(6)
<223> OTHER INFORMATION: n is a, c, g, or t

<400> SEQUENCE: 5
ggagcncagc cttcactgc                                                          19

<210> SEQ ID NO 6
<211> LENGTH: 18
<212> TYPE: DNA
<213> ORGANISM: artificial sequence
<220> FEATURE:
<223> OTHER INFORMATION: oligonucleotide ODN2c
<220> FEATURE:
<221> NAME/KEY: misc_feature
<222> LOCATION: (5)..(5)
<223> OTHER INFORMATION: n is a, c, g, or t

<400> SEQUENCE: 6
gagcncagcc ttcactgc                                                           18

<210> SEQ ID NO 7
<211> LENGTH: 19
<212> TYPE: DNA
<213> ORGANISM: artificial
<220> FEATURE:
<223> OTHER INFORMATION: oligonucleotide ODN2d
<220> FEATURE:
<221> NAME/KEY: misc_feature
<222> LOCATION: (13)..(13)
<223> OTHER INFORMATION: n is a, c, g, or t

<400> SEQUENCE: 7
ggagctcagc ctncactgc                                                          19

<210> SEQ ID NO 8
<211> LENGTH: 21
<212> TYPE: DNA
<213> ORGANISM: artificial sequence
<220> FEATURE:
<223> OTHER INFORMATION: oligonucleotide ODN2e
<220> FEATURE:
<221> NAME/KEY: misc_feature
<222> LOCATION: (1)..(1)
<223> OTHER INFORMATION: n is a, c, g, or t

<400> SEQUENCE: 8
ngtggatccg accgtggtgc c                                                       21

<210> SEQ ID NO 9
<211> LENGTH: 20
<212> TYPE: DNA
<213> ORGANISM: artificial sequence
<220> FEATURE:
<223> OTHER INFORMATION: oligonucleotide ODN2f
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 9
nggagctcag ccttcacngc                                                         20

<210> SEQ ID NO 10
<211> LENGTH: 19
<212> TYPE: DNA
<213> ORGANISM: artificial sequence
<220> FEATURE:
<223> OTHER INFORMATION: oligonucleotide ODN3a

```
<400> SEQUENCE: 10
ggagctcagc cttcactgc                                                    19

<210> SEQ ID NO 11
<211> LENGTH: 20
<212> TYPE: DNA
<213> ORGANISM: artificial sequence
<220> FEATURE:
<223> OTHER INFORMATION: oligonucleotide ODN3b

<400> SEQUENCE: 11
gtggatccga ccgtggtgcc                                                   20

<210> SEQ ID NO 12
<211> LENGTH: 20
<212> TYPE: DNA
<213> ORGANISM: artificial sequence
<220> FEATURE:
<223> OTHER INFORMATION: reverse primer

<400> SEQUENCE: 12
gtggatccga ccgtggtgcc                                                   20

<210> SEQ ID NO 13
<211> LENGTH: 19
<212> TYPE: DNA
<213> ORGANISM: artificial sequence
<220> FEATURE:
<223> OTHER INFORMATION: forward primer

<400> SEQUENCE: 13
ggagctcagc cttcactgc                                                    19

<210> SEQ ID NO 14
<211> LENGTH: 40
<212> TYPE: DNA
<213> ORGANISM: artificial sequence
<220> FEATURE:
<223> OTHER INFORMATION: oligonucleotide
<220> FEATURE:
<221> NAME/KEY: misc_feature
<222> LOCATION: (20)..(20)
<223> OTHER INFORMATION: n is a, c, g, or t

<400> SEQUENCE: 14
ggagctcagc cttcactgcn ggcaccacgg tcggatccac                              40

<210> SEQ ID NO 15
<211> LENGTH: 40
<212> TYPE: DNA
<213> ORGANISM: artificial sequence
<220> FEATURE:
<223> OTHER INFORMATION: oligonucleotide
<220> FEATURE:
<221> NAME/KEY: misc_feature
<222> LOCATION: (20)..(20)
<223> OTHER INFORMATION: n is a, c, g, or t

<400> SEQUENCE: 15
cctcgagtcg gaagtgacgn ccgtggtgcc agcctaggtg                              40

<210> SEQ ID NO 16
<211> LENGTH: 20
<212> TYPE: DNA
<213> ORGANISM: artificial sequence
<220> FEATURE:
<223> OTHER INFORMATION: oligonucleotide ODN2g
```

```
<220> FEATURE:
<221> NAME/KEY: misc_feature
<222> LOCATION: (1)..(1)
<223> OTHER INFORMATION: modification based on phosphoramidite

<400> SEQUENCE: 16
nggagctcag ccttcactgc                                               20

<210> SEQ ID NO 17
<211> LENGTH: 20
<212> TYPE: DNA
<213> ORGANISM: artificial sequence
<220> FEATURE:
<223> OTHER INFORMATION: oligonucleotide ODN2h
<220> FEATURE:
<221> NAME/KEY: misc_feature
<222> LOCATION: (1)..(1)
<223> OTHER INFORMATION: modification based on phosphoramidite

<400> SEQUENCE: 17
nggagctcag ccttcactgc                                               20

<210> SEQ ID NO 18
<211> LENGTH: 20
<212> TYPE: DNA
<213> ORGANISM: artificial sequence
<220> FEATURE:
<223> OTHER INFORMATION: oligonucleotide ODN2i
<220> FEATURE:
<221> NAME/KEY: misc_feature
<222> LOCATION: (1)..(1)
<223> OTHER INFORMATION: modification on phosphoramidite

<400> SEQUENCE: 18
nggagctcag ccttcactgc                                               20

<210> SEQ ID NO 19
<211> LENGTH: 19
<212> TYPE: DNA
<213> ORGANISM: artificial sequence
<220> FEATURE:
<223> OTHER INFORMATION: reverse primer

<400> SEQUENCE: 19
gcagtgaagg ctgagctcc                                                19
```

POST-SYNTHETIC MODIFICATION OF NUCLEIC ACIDS BY INVERSE DIELS-ALDER REACTION

This application is a continuation of PCT/EP2011/000491, filed Feb. 3, 2011; which claims the priority of EP Application No. 10001122.0, filed Feb. 3, 2010. The contents of the above-identified applications are incorporated herein by reference in their entirety.

REFERENCE TO SEQUENCE LISTING, TABLE OR COMPUTER PROGRAM

The Sequence Listing is concurrently submitted herewith with the specification as an ASCII formatted text file via EFS-Web with a file name of Sequence Listing.txt with a creation date of Jul. 25, 2012, and a size of 5 kilobytes. The Sequence Listing filed via EFS-Web is part of the specification and is hereby incorporated in its entirety by reference herein.

TECHNICAL FIELD

The present invention concerns a method and a kit for the post-synthetic modification of nucleic acids, preferably DNA, by inverse Diels-Alder reaction.

BACKGROUND OF THE INVENTION

Methods for labeling biomolecules with fluorescent dyes and affinity tags have become indispensable tools in the modern life sciences, and for those conjugation strategies it is important that they allow the site-specific post-synthetic coupling of complex molecules under mild conditions.

While for many years NHS ester chemistry dominated both protein and nucleic acid functionalization (G. T. Hermanson, Bioconjugate Techniques, *Academic Press*. San Diego, 1996), cycloaddition reactions have gained considerable importance. One of the most versatile post-synthetic labeling methods for DNA oligonucleotides is the copper(I)-catalyzed azide alkyne "click" reaction developed by Sharpless in 2001 (H. C. Kolb, M. G. Finn, K. B. Sharpless, Angew. Chem. 2001, 113, 2056-2075; Angew. Chem. Int. Ed. 2001, 40, 2004-2021). However, copper will be noxious for living cells above certain concentrations.

The first study on nucleic acid functionalization by Diels-Alder reaction used anthracene-modified oligonucleotides and maleimide dienophiles. While the reaction proceeded with high selectivity under mild conditions, the low reactivity required huge (>500-fold) excess of dienophile for appreciable product formation (B. Seelig, A. Jäschke, *Tetrahedron Lett.* 1997, 38, 7729-7732; b) B. Seelig, A. Jäschke, *Chem. Biol.* 1999, 6, 167-176). Consequently, only very few laboratories developed or applied normal electron demand Diels-Alder bioconjugations.

Since the aforementioned technologies have several disadvantages for labelling nucleic acid molecules, there is a further need for a method of post-synthetic modification of nucleic acids, preferably DNA, which is easy, cheap and works reliable also when larger nucleic acid molecules have to be labelled. Such a method should be suitable for small chemically synthesized oligonucleotides as well as for longer enzymatically amplified DNA strands.

SUMMARY OF THE INVENTION

The inventors discovered that such an improved method of post-synthetic modification of nucleic acids, preferably DNA, may be based on a Diels-Alder reaction with inverse electron demand. In general, a Diels-Alder reaction with inverse electron demand (in the following "inverse Diels Alder reaction") takes place between an electron-rich dienophile and an electron-deficient diene (J. Sauer, D. Lang, D. Peter, *Chem. Ber.* 1964, 76, 603).

The inventors developed the inverse Diels-Alder reaction as a bioorthogonal reaction for labeling oligonucleotides in a highly selective and efficient way. The method of the present invention is characterized by the introduction of norbornene or trans-cyclooctene moieties, which are reactive in inverse Diels-Alder reactions into oligonucleotides at various positions by solid-phase synthesis. After cleavage from the resin and deprotection, inverse Diels-Alder reactions are conducted using water-stable tetrazines:

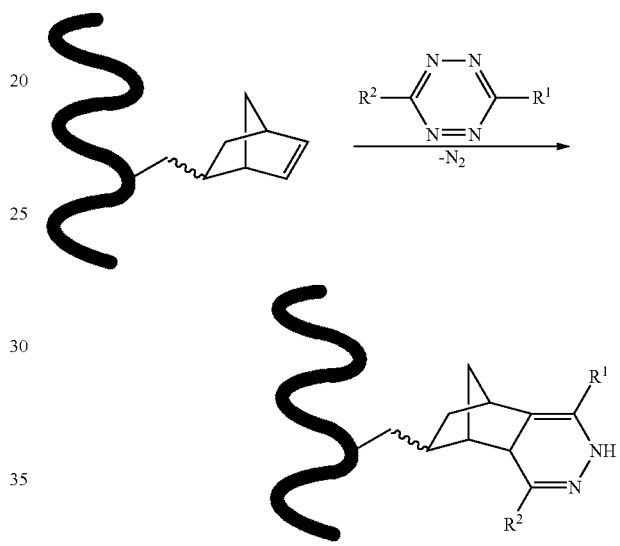

$R^1/R^2$ = aryl, heteroaryl

DNA strands carrying a dienophile undergo inverse Diels-Alder reaction with an electron-deficient tetrazine diene. The cycloaddition is shown to be selective and highly efficient. The dienophile may be a norbornene or trans-cyclooctene moiety.

$R^1$ and $R^2$ may be the same or different.

"Aryl" means any aromatic monocyclic or multicyclic ring systeme with 6 to 14 carbon atoms, preferably 6 to 10 carbon atoms. The aryl groups may be substituted with one or more substituents (e.g. C1-C12 alkyl, OH, halogen, etc.) Preferred aryl groups are phenyl or naphthyl.

"Heteroaryl" means any aromatic moncyclic or multicyclic ring system with 5 to 14 ring atoms wherein one or more ring atoms are different from C, e,g, N, S or O. Preferred heteroaryls are pyridyl, pyrazinyl, thienyl or, furanyl.

The method of the present invention (FIG. 1) comprises:
(a) Preparation of oligonucleotides modified by norbornene or trans-cyclooctene
   The oligonucleotides may be modified either terminally (3' or 5') or internally
(b) Preparation of modified tetrazines, preferably modified with a label or a marker such as, for example, fluorescent, luminescent or phosphorescent dyes, or affinity tags
(c) Reaction of the modified oligonucleotides of step (a) with the modified tetrazines via inverse Diels Alder reaction.

Examples of fluorescent, luminescent or phosphorescent dyes are dansyl, fluorescein, acridine, rhodamine and cyanine dyes.

Examples of affinity tags are biotin, the His-tag, the Flag-tag or the strep-tag.

Any tetrazine known by a person skilled in the art may be used. Examples of suitable tetrazines are shown below and in FIG. 2 although the invention shall not be restricted to only those.

The oligonucleotide may have any length between 3 and 10000 nucleotides, preferably between 4 and 5000 nucleotides, more preferably between 5 and 1000 nucleotides or between 10 and 500 nucleotides, most preferably between 10 and 200 nucleotides. In a particular embodiment of the invention the oligonucleotide to be modified by the method of the present invention may have more than 50, preferably more than 100 nucleotides. The oligonucleotide according to the invention may by single-stranded or double-stranded DNA or RNA as well as nucleic acid analogs (e.g. PNA, LNA) or chimera of these with DNA and/or RNA. In addition, enyzmatically modified PCR products may be used. It is an advantage of the present invention that such large molecules of nucleic acids can be modified by the method of the invention.

Preferably, one, two or three, i.e. up to three, modifications per oligonucleotide can be introduced efficiently. Any type of nucleotide of the oligonucleotide may be modified, preferably thymidine and/or guanine. It is possible to bring different labels in one oligonucleotide strand, i.e. to have the 3- and/or 5-end of the oligonucleotide labelled and/or to contain (additionally) an internal modification within the oligonucleotide on a nucleotide of the oligonucleotide which is not at the 3'- or 5'-end of said oligonucleotide. All combinations of 3'/5'/internally are possible. In a preferred embodiment of the invention 2, 3, 4, 5 or more nucleotides of the oligonucleotide are modified by the method according to the invention. In a particular embodiment of the invention 2, 3, 4, 5 or more nucleotides of the oligonucleotide are modified with the same label.

The inverse Diels Alder reaction between the modified oligonucleotide according to the present invention and the modified tetrazin uses preferably equimolar amounts of both components if the oligonucleotide is below 100 nucleotides. For larger nucleic acids stretches, however, the tetrazine is used in 2-20-fold excess, preferably 5-10-fold excess, over the dienophile-modified oligonucleotide. The reaction takes place between 0 and 100° C., preferably between 20-40° C., preferably at room temperature. The reaction may take place in any suitable media, preferably in aqueous media.

In an embodiment of the invention oligonucleotides modified with norbornene or trans-cyclooctene moieties according to the present invention can be converted to the Diels-Alder product at low concencentrations of about least 500 µM, preferred of about at least 250 µM, most preferred of about least 100 µM with about equimolar amounts of tetrazine.

In a further aspect of the invention yields of at least 60%, preferably at least about 80%, most preferred at least about 90% of the Diels-Alder product can be obtained by oligonucleotides modified with norbornene or trans-cyclooctene moieties converted with tetrazin. In a preferred embodiment such yields of at least 60%, preferably at least about 80%, most preferred at least about 90% can be obtained by conversions applying equimolar amounts of tetrazine and modified oligonucleotides. For example, an oligonucleotide according to the invention in a concentration of about 170 µM can be converted with an equimolar amount of tetrazine yielding about 80% of the Diels-Alder product.

It is preferred that dienophiles according to the invention, i.e. norbornene or trans-cyclooctene moieties, do not contain a terminal double bound.

Accordingly, high yields of Diels-Alder products can be obtained by the method of the invention converting oligonucleotides modified with norbornene or trans-cyclooctene moieties with, preferably equimolar amounts, of tetrazine. Only equimolar amounts or low excess of tetrazine are sufficient to high yields of the Diels-Alder product. The tetrazine may be modified, e.g. substituted, with one or more substitutents selected from the group consisting of amino acids, peptides or oligonucleotides. Besides, labels or markers may be conjugated or bound to the tetrazine. Such labels or markers may be selected from the group consisting of pharmaceutical, therapeutical or diagnostic compound; dyes, e.g. fluorescent, luminescent or phosphorescent; radiolabels, affinity tags.

In addition, the present invention concerns a kit for the post-synthetic modification of nucleic acids comprising at least one of the above identified phosphoramidites 1, 2, 3, the modified support 4, 8, 9 or 10 and at least one of the above identified modified tetrazines 5, 6 or 7.

BRIEF DESCRIPTION OF THE FIGURES

FIG. 2 shows Tetrazin compounds.

FIGS. 7a-7l show HPLC chromatograms of the purified oligonucleotides of Table S1 (for ODN 1a-c; ODN 2a-f)

Gradients used for HPLC-analysis:
ODN1a-c: Increase from 1% to 45% buffer B (ACN) over 45 min.
ODN2a-d and ODN3a: 10 min 20% buffer B (MeOH), increase to 50% buffer B (MeOH) over 30 min.
ODN2e-f and ODN 3b: 10 min 10% buffer B (ACN), increase to 40% buffer B (ACN) over 30 min.

FIGS. 8a-8d show HPLC chromatograms of the performed Inverse Diels Alder reactions of Table S2.

Figure 8A:
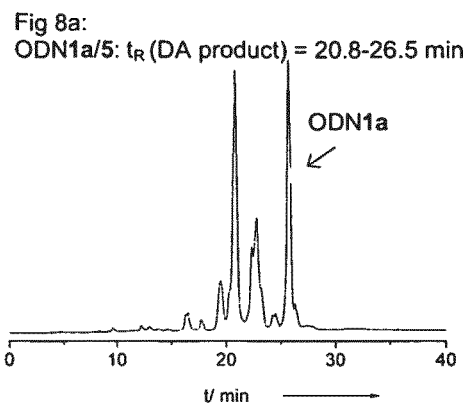
Figure 8B:
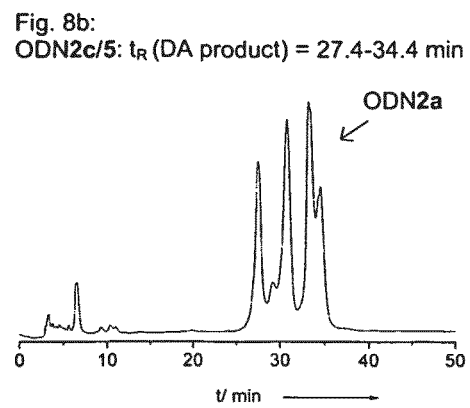
Figure 8C:
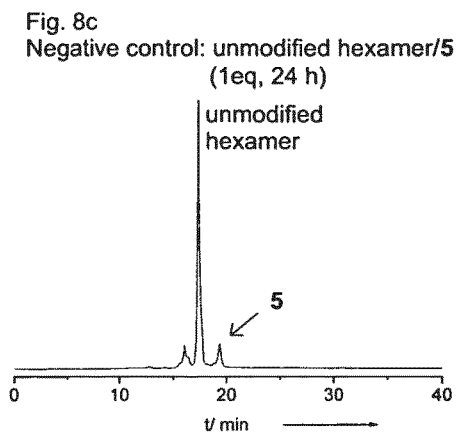
Figure 8D:
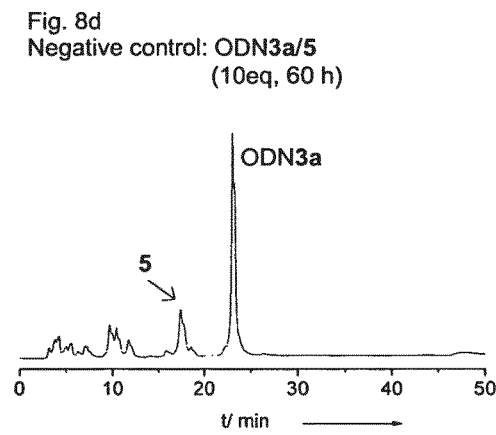

FIG. 8a: HPLC chromatograms for Inverse DA reaction between ODN 1a/5 and FIG. 8c: corresponding negative control FIG. 8b: HPLC chromatograms for Inverse DA reaction between ODN 2c/5 and FIG. 8d: corresponding negative control Gradients used for HPLC analysis:
ODN1a-c: Increase from 1% to 45% buffer B (ACN) over 45 min.
ODN2a-d/tetrazine 5: 5 min 25% buffer B (MeOH), increase to 45% buffer B (MeOH) over 40 min.
ODN2a-f/tetrazine 6: 10 min 50% buffer B (MeOH), increase to 70% buffer B (MeOH) over 20 min.

FIG. 9 shows MALDI-TOF analysis for the obtained DA products of Table S2.

FIG. 10 shows HPLC chromatograms for inverse DA reaction between ODN1a and tetrazine 5 at RT (left) and 80° C. (right).

FIG. 11 shows 2% agarose gel of PCR mixtures, stained with ethidium bromide

The designation of the lanes indicates the oligonucleotide used as forward and reverse primer.

Figure 12:
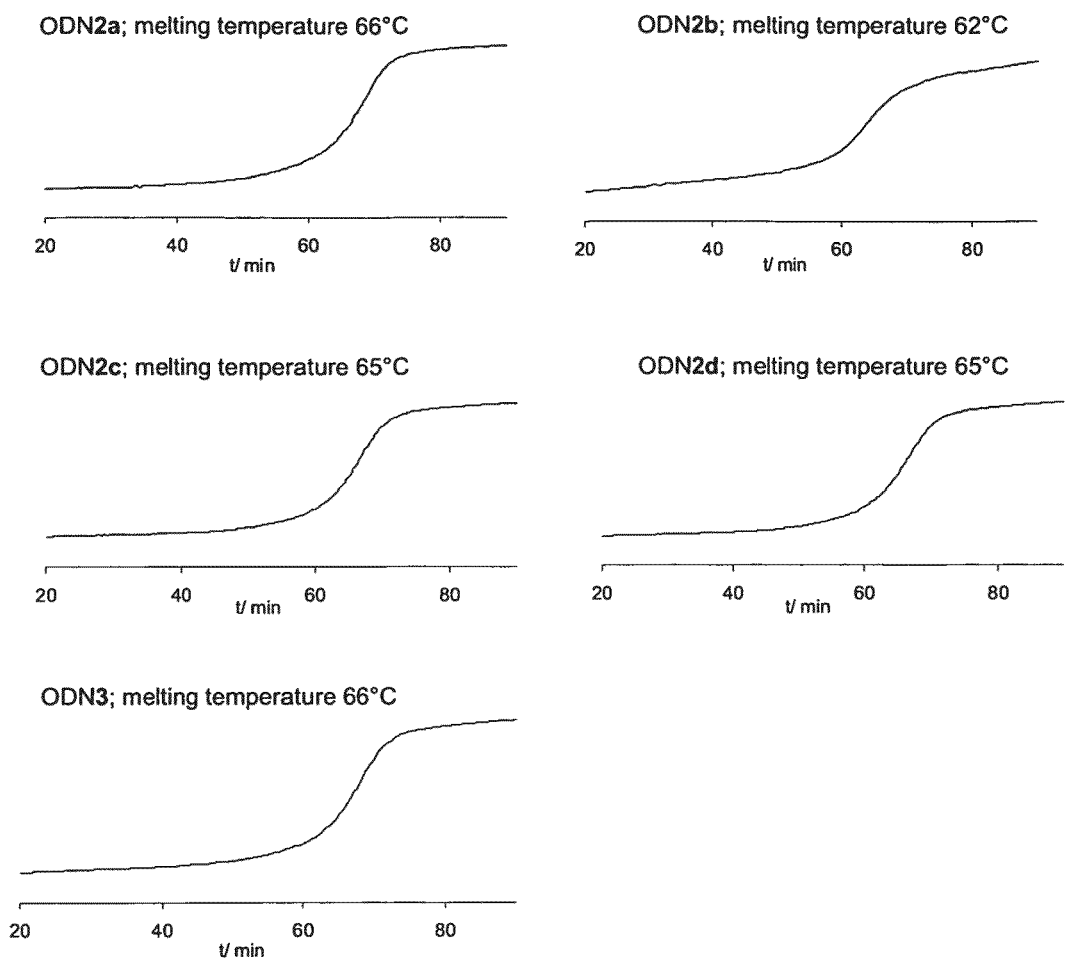

FIG. 12 shows normalized thermal denaturation curves for the DNA duplexes of 19mers cited in Table S1 and reverse primer (SEQ ID NO:19, 5'-GCA GTG AAG GCT GAG CTC C-3').

Figure 13:
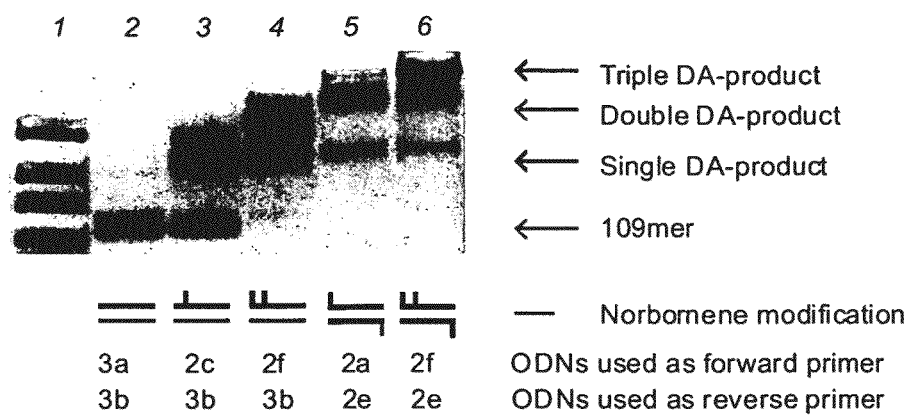

FIG. 13 shows 2% agarose gel (stained with ethidium bromide) for inverse Diels-Alder reaction between modified double-stranded 109 mer PCR products (c=1.52 µM) and tetrazine 7 at room temperature. The tetrazine was used in 10-fold excess per dienophilic modification, and the reaction mixture treated with 1 eq of streptavidin before loading.

lane 1: ultra low range DNA ladder
lane 2: unmodified 109mer
lane 3: single-modified 109mer
lanes 4-5: double-modified 109mer
lane 6: triple-modified 109mer

DETAILED DESCRIPTION OF THE INVENTION

In a preferred embodiment, norbornene phosphoramidite 1 was synthesized starting form bicyclo[2.2.1]hept-2-en-2-carbaldehyde for the selective modification of the 5'-terminus of an oligonucleotide. In further preferred embodiments phosphoramidites 2 and 3 served as building blocks for internal modification of DNA. The preparation of phoshoramidites 1 and 2 is shown in the below examples. Phosphoramidite 3 is prepared according to Gutsmiedl et al., Org. Lett 2009, 11, 2405-2408. Solid support 4, prepared by standard procedures, finally allowed selective 3'-derivatization: In general, the solid support may be any suitable support material or matrix, e.g. glass (particularly glass beads), sheets or membranes of polypropylene, nylon, cellulose, cellulose derivatives, polyether sulfones, polyamides, PVC, PVDF, polyester, Teflon, polyethylene, etc. The solid support may be derivatized with functional groups, e.g. hydroxyl, amino, carboxyl, etc.

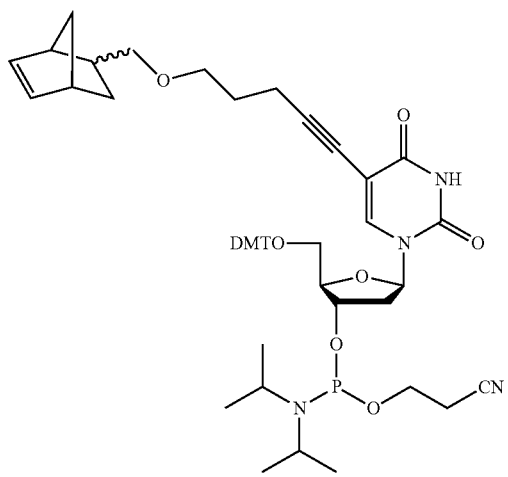

2

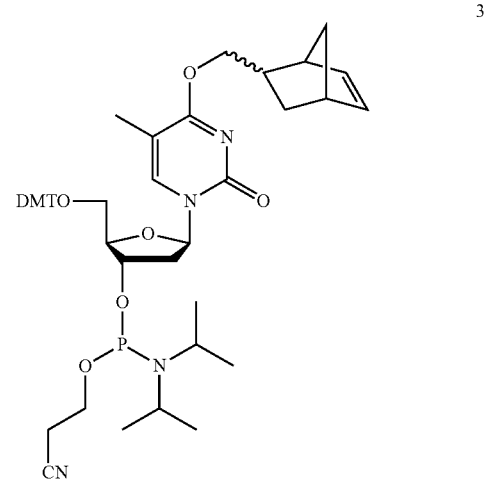

3

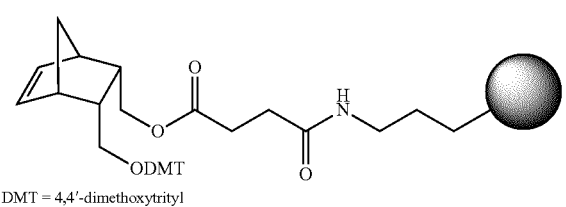

4

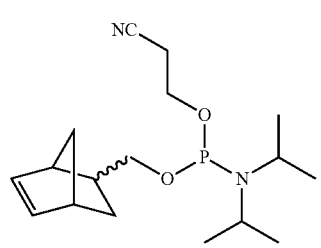

DMT = 4,4'-dimethoxytrityl

Phosphoramidites 1-3 as well as solid support 4 are then incorporated into or bound to an oligonucleotide. Details of this reaction are described in the examples.

In the following Table 1 exemplary oligonucleotides are shown. These oligonucleotides are not construed to be any limitation of the invention.

TABLE 1

Oligodeoxynucleotides (ODNs)

| ODN | Sequence[a] |
|---|---|
| ODN1a | 5'-WTGCTCA-3'<br>(SEQ ID NO: 1) |
| ODN1b | 5'-TGCXTCA-3'<br>(SEQ ID NO: 2) |

TABLE 1-continued

Oligodeoxynucleotides (ODNs)

| ODN | Sequence[a] |
|---|---|
| ODN1c | 5'-TGCTCAZ-3' (SEQ ID NO: 3) |
| ODN2a | 5'-WGGAGCTCAGCCTTCACTGC-3' (SEQ ID NO: 4) |
| ODN2b | 5'-GGAGCXCAGCCTTCACTGC-3' (SEQ ID NO: 5) |
| ODN2c | 5'-GGAGCYCAGCCTTCACTGC-3' (SEQ ID NO: 6) |
| ODN2d | 5'-GGAGCTCAGCCTYCACTGC-3' (SEQ ID NO: 7) |
| ODN2e | 5'-WGTGGATCCGACCGTGGTGCC-3' (SEQ ID NO: 8) |
| ODN2f | 5'-WGGAGCTCAGCCTTCACYGC-3 (SEQ ID NO: 9) |
| ODN2g | 5'-W₁GGAGCTCAGCCTTCACTGC-3' (SEQ ID NO: 16) |
| ODN2h | 5'-W₂GGAGCTCAGCCTTCACTGC-3' (SEQ ID NO: 17) |
| ODN2i | 5'-W₃GGAGCTCAGCCTTCACTGC-3' (SEQ ID NO: 18) |
| ODN3a | 5'-GGAGCTCAGCCTTCACTGC-3' (SEQ ID NO: 10) |
| ODN3b | 5'-GTGGATCCGACCGTGGTGCC-3 (SEQ ID NO: 11) |

[a]W = Modification based on phosphoramidite 1, W₁ = Modification based on phosphoramidite 8, W₂ = Modification based on phosphoramidite 9, W₃ = Modification based on phosphoramidite 10, X = DNA nucleotide based on phosphoramidite 2, Y = DNA nucleotide based on phosphoramidite 3, Z = Modification based on support 4. ODN3a and ODN3b are controls.

As a second binding partner of the inverse Diels Alder cycloaddition a tetrazine is synthesized according to known chemical methods (Braun et al., Drug Des. Dev. Ther. 2008, 2, 289-301; Pipkorn et al., Pept. Sci. 2009, 15, 235-241) Preferred tetrazins are shown in FIG. 2 whereas the shown acid function may be derivatized by e.g. an ester or amide function. In a particular preferred embodiment, tetrazine 5 was synthesized as an universal building block that allows easy derivatization by amine nucleophiles. Following this synthetic route, dansyl tetrazine 6 and biotin tetrazine 7 were synthesized (Braun et al. (2008), Pipkorn et al., 2009). These compounds are to be understood as exemplary compounds carrying a label. For example any fluorescent, luminescent or phosphorescent dye or any other affinity tag may be bound to the tetrazine to allow labelling or tagging of the oligonucleotide after the following inverse Diels Alder reaction.

Although the present invention shall not be restricted to any length of oligonucleotide or use of any suitable tetrazine, in the following the coupling reaction via inverse Diels Alder reaction is shown on hexa- and heptanucleotides modified either terminally or internally (c.f. Table 1).

First, the oligonuclotide (e.g. ODN1a-2d) is treated with tetrazine (e.g. tetrazine 5, 6 or 7) in aqueous solution in 1:1 stoichiometry. After 0.5-24 hours, preferably about 3-20 hours, more preferably about 5-17 hours, reaction time, decolouration of the solution will be observed. The conversion to the Diels-Alder product may be examined with any suitable method, e.g. HPLC. Results of the inverse Diels Alder reactions are shown in Table 2.

Figure 1:
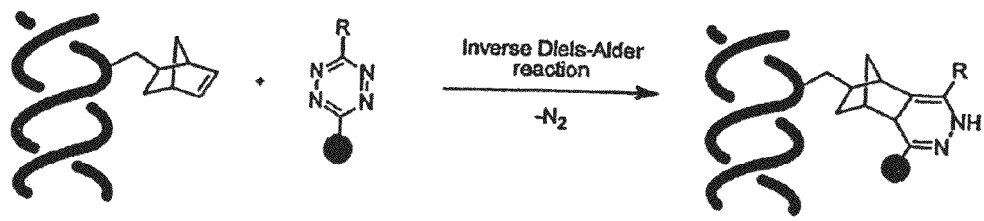
FIG. 1 shows New route for labeling DNA. DNA strands carrying a dienophile undergo inverse Diels-Alder reaction with an electron-deficient tetrazine diene.
Figure 3:
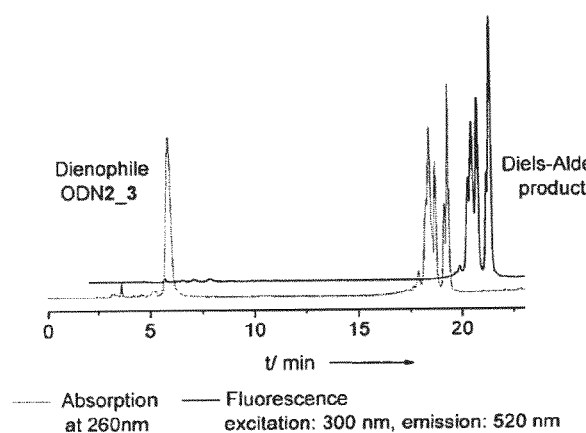
FIG. 3 shows HPLC-Chromatogram of the inverse Diels-Alder reaction between ODN2c and tetrazine 6 after 30 min reaction time. Absorption at 260 nm: lower graph; fluorescence (excitation: 300 nm; emission: 520 nm): upper graph.

Although short oligonucleotides (e.g. internally modified ODN1b and 3'-modified ODN1c products) allow easy analytical characterization, exemplary 19mers ODN2a-d (Table 1) incorporating phosphoramidites 1-3 were prepared to study their suitability as primers in polymerase chain reactions (PCR). Thermal denaturation analysis with ODN2a, c, d and non-modified ODN3 showed that the norbornene modification had no significant influence on the duplex stability of DNA. To study their reactivity in inverse Diels-Alder reactions, exemplary ODN2a-d (c=100 µM) were treated with about equimolar amounts of tetrazine 5 or 6. After six hours reaction time at room temperature, HPLC and MALDI-TOF analysis indicated a positive reaction for all synthesized oligonucleotides (Table 2, entries 5-11). The reaction products were obtained in good to excellent yields with the internally modified ODN2b-d showing a higher reactivity than terminally derivatized ODN2a (Table 2). Increasing concentration and reaction time yielded higher conversions up to 82% (Table 2, entries 5-6 and 10-11). A control experiment of non-modified ODN3a with tetrazine 5 and 6 showed no reaction, even after 60 hours reaction time and using tetrazine in 10-fold excess. FIG. 3 shows a typical HPLC chromatogram for a positive inverse Diels-Alder reaction with 6 as diene. Due to the isomeric variety of the Diels-Alder products there is always more than one product peak appearing in the HPLC-chromatogram. The relative intensity of the peaks is temperature-dependent in accordance with the endo-rule.

TABLE 2

Performed Diels-Alder reactions.[a]

| Entry | Dienophile | Diene (Equivalents) | Reaction time [h] | Conversion [%][b] |
|---|---|---|---|---|
| 1 | ODN1a | 5 (1) | 1 | 73 |
| 2 | ODN1a | 6 (1) | 1 | 46 |
| 3 | ODN1b | 5 (1) | 17 | 96 |
| 4 | ODN1c[c] | 5 (3) | 17 | 94 |
| 5 | ODN2a | 5 (1) | 6 | 42 |
| 6 | ODN2a | 5 (1) | 24 | 74 |
| 7 | ODN2b | 5 (1) | 3.5 | 53 |
| 8 | ODN2c | 5 (1) | 6 | 71 |
| 9 | ODN2d | 5 (1) | 6 | 73 |
| 10 | ODN2d | 6 (1) | 6 | 54 |
| 11 | ODN2d | 6 (1) | 6 | 82 |
| 12 | ODN3a | 6 (2) | 60 | 0 |
| 13 | ODN3a | 5 (10) | 60 | 0 |

[a]ODN2a-d and ODN3a (control) were used as 100 µM (entry 5-10 and 12-13) or 300 µM (entry 11), ODN1a as 700 µM, ODN1b as 133 µM and ODN1c as 250 µM aqueous solution.
[b]Determined by integration of the HPLC trace at 260 nm after inverse Diels-Alder reaction.
[c]DMT-ON product.

Figure 4:
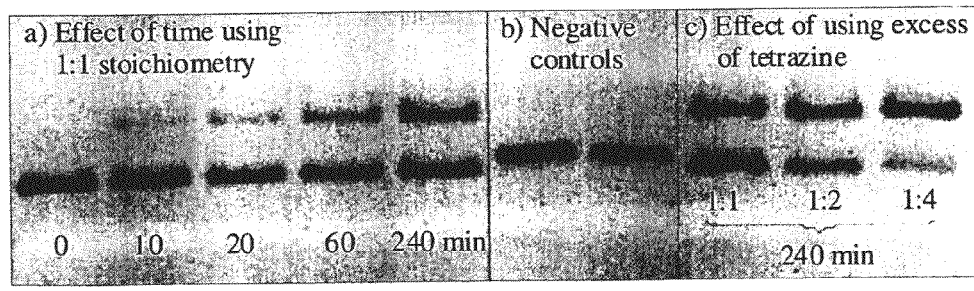
FIG. 4 shows 2% Agarose gel (stained with ethidium bromide) for inverse Diels-Alder reaction between a 5'-modified double-stranded 109-mer PCR products (c=3.47 µM) and tetrazine 7 at room temperature. Reaction mixture treated with streptavidin before loading. For negative controls unmodified dsDNA was treated with either 2 (left) or 10 (right) equivalents of 7 for 15 hours at room temperature.

Site-specific modification procedures are most useful when they can be applied to really large (e.g. enzymatically assembled) biomolecules. To investigate the utility of the method of the present invention, a dienophile-carrying double-stranded 109mer DNA has been amplified by PCR, using a double-stranded template and dienophile-modified oligonucleotide (e.g. ODN2a-d) as primer. PCR yielded a clean product which was then reacted with a labelled tetrazine (e.g. biotin-tetrazine 7). The labelled tetrazine is used in 2-20-fold excess, preferably 5-10-fold excess, over the dienophile-modified oligonucleotide. After reaction at 20-30° C., preferably at room temperature, aliquots were withdrawn, mixed with the biotin-binding protein streptavidin if the tetrazine was biotin-labelled, and loaded onto an agarose gel where the bound protein caused a strong retardation of the DNA. Reference is made to FIG. 4 which shows the respective experiment carried out with a 10-fold excess of 7 over the dienophile-carrying 109mer duplex. After 10 minutes (lane 4), a faint product band is already visible, and after 150 minutes, about 65% of the DNA is found to be biotinylated (lane 10). A control experiment with unmodified DNA (same sequence, prepared by PCR using ODN3 as primer) shows no reaction at all, even with a 100-fold excess of 7 and 180 minutes reaction time (lane 13).

In another embodiment of the present invention, E-cyclooctene-based phosphoramidite 8, cyclopropano-norbornene based phosphoramidite 9 and cyclobutene-bicyclooctene building block 10 (ODN2i) were synthesized, which surprisingly showed a significant further increased reaction rate of the inverse Diels-Alder reaction. They were successfully incorporated into a DNA strand (ODN2g-h) via solid-phase synthesis using anhydrous tert-butylhydroperoxide as oxidizing reagent. With the application of compound 8 it is possible to obtain good conversion rates at even low concentrations, e.g. 1 µM, and with about equimolar amounts of tetrazine. Finally, cyclobutene-bicyclooctene building block 10 (ODN2i) offers the possibility to introduce two different labels using the cycloaddition reaction due to the two dienophil units in the structure of 10.

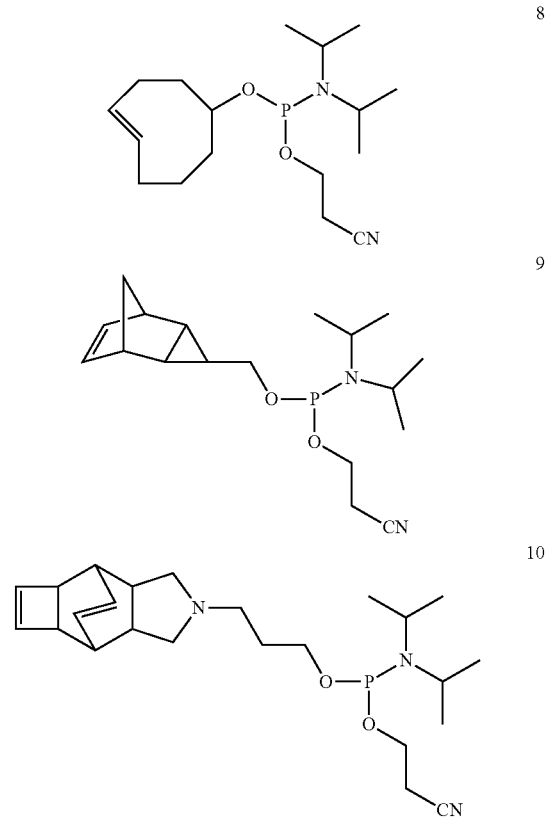

TABLE 3

Performed Diels-Alder reactions

| Entry | Dienophile[a] | Diene (Equivalents) | Reaction time [h] | Conversion [%][b] |
|---|---|---|---|---|
| 1 | ODN2a | 6 (1) | 1 | 80 |
| 2 | ODN2g | 6 (1) | 1 | 86 (98) |
| 3 | ODN2h | 6 (1) | 1 | 89 |
| 4 | ODN2i | 6 (0.5) | 1 | 30 |
| 5 | ODN2i | 6 (1) | 1 | 71 |

[a]Oligonucleotides were used at a concentration of 170 μM
[b]Determined by integration of the HPLC trace at 260 nm after Diels-Alder reaction.

In the present application it has been clearly demonstrated that the inverse electron demand Diels-Alder reaction is a highly efficient and chemoselective method for the post-synthetic modification of nucleic acids, in particular DNA. The method is suitable for small chemically synthesized oligonucleotides as well as for longer enzymatically amplified DNA strands for both singly and multiply modified oligonulecotides. Compared to other post-synthetic labeling strategies, inverse Diels-Alder conjugation works efficiently at low reactant concentration and often with only equimolar amounts of labeling reagent. The reaction proceeds smoothly under mild conditions, and no transition metals or other potentially damaging additives are required. Because no transition metals are required, the Diels-Alder products according to the invention can be advantageously applied in living cells. These properties render the method attractive for conjugating expensive and sensitive compounds. With the present invention it is possible to achieve the otherwise very difficult 5' labelling at a solid phase in a very elegant way. With the present invention it is furthermore possible to bring different labels in one oligonucleotide strand, i.e. to have the 3- and/or 5-end of the oligonucleotide labelled and/or to contain (additionally) an internal modification on a nucleotide which is not the 3'- or 5'-terminal nucleotide of the oligonucleotide. All combinations of 3'/5'/internally are possible.

The following Examples illustrate the invention and are not to be construed as limitations of the invention.

EXAMPLES

Example 1

General Materials and Methods

All reagents were purchased from Acros or Sigma-Aldrich and used without further purification. TLC was carried out on silica gel plates Polygram Sil G/UV$_{254}$ (40×80 mm) from Macherey-Nagel. Flash chromatography was carried out on silica gel 40-63 μm from J. T. Baker. Reversed-phase HPLC analyses was performed on a Agilent 1100 Series HPLC system equipped with a diode array detector and a fluorescence detector using a Phenomenex Luna C18 5 μm column (4.6×250 mm) and eluting with a gradient of 100 mM triethylammonium acetate (TEAA) pH 7.0 (buffer A) and 100 mM TEAA in methanol or acetonitrile (buffer B) at a flow rate of 1 ml/min. HPLC purification was performed with a semi-preparative column using a flow rate of 5 ml/min. NMR spectra were recorded on a Varian Mercury Plus 300 MHz spectrometer. FAB and EI mass spectra were recorded on a JEOL JMS-700 sector field mass spectrometer. MALDI mass spectra were recorded on a Bruker Biflex III using either DHB or 3-HPA as matrix. Oligonucleotide Synthesis was performed on an Expedite™ 8909 System automated Synthesizer using standard reagents from Sigma Aldrich Proligo. Agarose gels were stained with ethidium bromide and visualized by UV using an Alphalmager™ 2200. For desalting oligonucleotides Zip tip$_{C18}$ purchased from Millipore were used.

List of abbreviations used in the synthetic procedures: TEA=triethylamine, DMAP=4-dimethylaminopyridine, RT=room temperature, DMT=4,4'-dimethoxytrityl, CPG=controlled pore glass, DMF=dimethylformamide, ACN=acetonitrile, min=minutes, DA=Diels-Alder.

Example 2

Synthesis of Bicyclo[2.2.1]hept-2-en-2-ylmethyl 2-cyanoethyl-diisopropyl-phosphor-amidite (1)

To a solution of (exo/endo)-bicyclo[2.2.1]hept-2-en-2-yl-methanol (prepared according to J. M. Blanco, F. Fernández, X. Garcia-Mera, J. E. Rodríguez-Borges, Tetrahedron 2002, 58, 8843) [493 mg, 3.97 mmol] in 10 ml of acid free CH$_2$Cl$_2$ under argon diisopropylethylamine (2.17 ml, 12.6 mmol, 3.2 eq) was added. The mixture was cooled to 0° C. and 2-cyanoethyl-N,N-diisopropylchlorophosphoramidite (1.00 g, 4.19 mmol, 1.05 eq) was added. After stirring for one hour at RT the reaction mixture was directly loaded on a silica column. Purification by flash chromatography (hexane/ethyl acetate 95:5, 1% TEA) yielded the clean product as yellow oil (1.00 g, 3.08 mmol, 78%) in an exo/endo ratio of 1:4.

$^1$H-NMR (500 MHz, CDCl$_3$, 25° C., TMS): δ=0.48 (ddd, $^2$J=1.70 Hz, $^3$J=4.56 Hz, 2.75 Hz, 1H$_{endo}$), 1.14-1.18 (m, 4H$_{exo/endo}$), 1.23 (d, $^3$J=7.16 Hz, 1H$_{endo}$), 1.21-1.30 (m, 5H$_{exo}$), 1.41 (d, $^3$J=7.16 Hz, 1H$_{endo}$), 1.75-1.78 (m, 1H$_{endo}$), 2.32-2.40 (m, 1H$_{endo}$), 2.60-2.64 (m, 4H$_{exo/endo}$), 2.75-2.95 (m, 4H$_{exo/endo}$), 3.11-3.43 (m, 4H$_{exo/endo}$), 3.53-3.61 (m, 4H$_{exo/endo}$), 3.76-3.88 (m, 4H$_{exo/endo}$), 5.89 (ddd, $^3$J=8.86 Hz, 5.70 Hz, $^4$J=2.90 Hz, 1H$_{endo}$), 6.04-6.09 (m, 2H$_{exo}$), 6.11 (dd, $^3$J=5.70 Hz, 3.03 Hz, 1H$_{endo}$). $^{13}$C-NMR (75 MHz, CDCl$_3$, 25° C., TMS) δ=20.4, 24.6, 28.9, 29.5, 40.2, 41.5, 42.2, 43.0, 43.5, 43.8, 44.9, 49.3, 58.2, 67.1, 68.1, 117.6, 132.3, 136.5, 136.8, 137.3. $^{31}$P-NMR (121 MHz, CDCl$_3$, 25° C., H$_3$PO$_4$) δ=147.2 (d, J=46.6 Hz, endo), 147.4 (d, J=22.10 Hz, exo). MS (FAB$^+$): m/z 324.1 (calculated for [C$_{17}$H$_{29}$N$_2$O$_2$P$_1$]$^+$ 324.1).

Example 3

Synthesis of O$^4$-(Bicyclo[2.2.1]hept-2-en-2-ylmethyl)-5'-O-(4,4'-dimethoxytrityl)-2'-desoxythymidine-3'-O—[O-(2-cyanoethyl)-N,N'-diisopropylphosphoramidite] (2)

First, compound 2a was synthesized according to published procedures (.A. Heckel, Current Protocols in Nucleic Acid Chemistry 2007, 29, 1.17.1-1.17.6).

Figure 5:
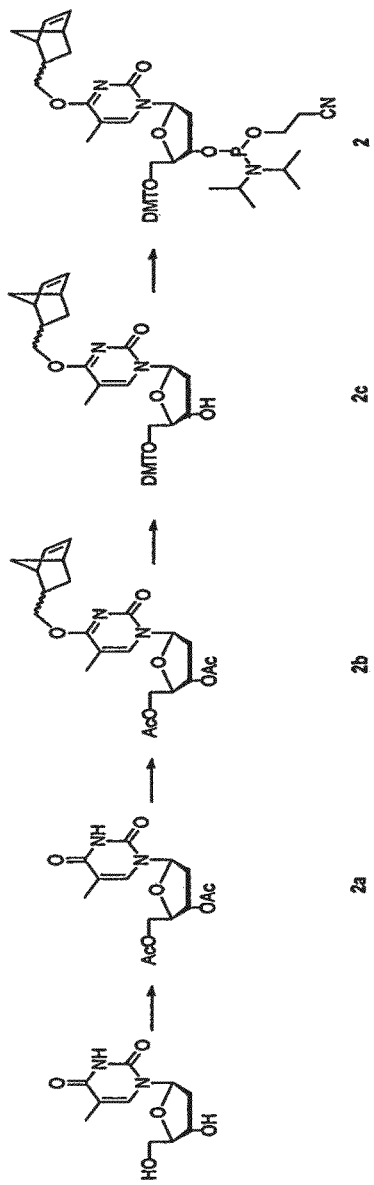
FIG. 5 shows reaction Scheme to prepare Compound 2

The synthesis scheme is shown in FIG. 5.

To prepare 3'-, 5'-Diacetyl-O$^4$-bicyclo[2.2.1]hept-2-en-2-ylmethyl-thymidine (2b), 1.09 ml of TEA was added to a solution of 2a (1.28 g, 3.93 mmol) and DMAP (0.96 g, 7.82 mmol) in 17.1 ml of ACN. After stirring the mixture for 10 min at RT triisopropylbenzylsulfonylchloride (2.39 g, 7.82 mmol) was added followed by an additional stirring for 4 h. To the obtained yellow mixture a solution of 1 (1.46 g, 11.7 mmol) in 1.64 ml TEA was added and the reaction mixture was stirred at RT for 14 h. For workup, 170 ml CHCl$_3$ and 170 ml H$_2$O were added and the aqueous phase extracted twice with CHCl$_3$. The combined organic phases were washed with 1M HCl and NaHCO$_3$-solution and dried over Na$_2$SO$_4$. After evaporation of the solvent and flash chromatopraphy (hexane/ acetone 3:1) 2c (340 mg, 0.79 mmol, 20%) was obtained as a yellow oil in an exo/endo ratio of 1:4.

$^1$H-NMR (500 MHz, CDCl$_3$, 25° C., TMS): δ=0.62 (ddd, $^2$J=11.73 Hz, $^3$J=4.37 Hz, 2.51 Hz, 1H$_{endo}$) 1.21-1.35 (m, 6H$_{exo/endo}$), 1.46 (ddd, $^2$J=8.11 Hz, $^3$J=4.04 Hz, 1.93 Hz, 1H$_{endo}$), 1.87 (ddd, $^2$J=11.73 Hz, $^3$J=9.24 Hz, 3.83 Hz, 1H$_{endo}$), 1.98 (d, $^4$J=1.07 Hz, 6H$_{exo/endo}$), 2.01-2.07 (m, 2H$_{exo/endo}$), 2.10-2.11 (m, 12H$_{exo/endo}$), 2.51-2.57 (m, 1H$_{endo}$), 2.69 (ddd, $^2$J=14.22 Hz, $^3$J=5.50 Hz, 2.08 Hz, 2H$_{exo/endo}$), 2.75-2.95 (m, 4H$_{exo/endo}$), 3.95 (dd, $^2$J=10.81 Hz, $^3$J=9.85 Hz, 1H$_{endo}$) 4.19 (dd, $^2$J=10.81 Hz, $^3$J=6.61 Hz, 1H$_{endo}$), 4.28 (td, $^3$J=6.36 Hz, 3.05 Hz, 2H$_{exo/endo}$), 4.33-4.39 (m, 1H$_{exo}$), 4.36 (d, $^2$J=3.97 Hz, 4H$_{exo/endo}$), 4.48 (ddd, $^2$J=10.91 Hz, $^3$J=6.49 Hz, J=4.93 Hz, 1H$_{exo}$), 5.20 (td, $^3$J=6.36 Hz, 2.11 Hz, 2H$_{exo/endo}$), 5.93 (dd, $^3$J=5.63 Hz, 2.94 Hz, 1H$_{endo}$) 6.08-6.12 (m, 2H$_{exo}$), 6.15 (dd, $^3$J=5.64 Hz, 3.00 Hz, 1H$_{endo}$), 6.35 (dd, $^3$J=8.23 Hz, 5.50 Hz, 2H$_{exo/endo}$), 7.50 (d, $^4$J=1.07 Hz, 2H$_{exo/endo}$). $^{13}$C-NMR (75 MHz, CDCl$_3$, 25° C., TMS): δ=12.4, 20.8, 20.9, 28.8, 29.5, 37.6, 37.8, 38.6, 41.6, 42.2, 43.6, 43.9, 45.0, 49.3, 63.8, 70.9, 71.6, 74.2, 82.4, 86.4, 105.1, 132.1, 136.2, 137.0, 137.6, 138.1, 155.8, 170.1, 170.4, 170.5. MS (FAB$^+$): m/z 433.2 (calculated for [(C$_{22}$H$_{28}$N$_2$O$_{7+}$H)]$^+$ 433.2).

To prepare O$^4$-(Bicyclo[2.2.1]hept-2-en-2-ylmethyl)-5'-O-(4,4'-dimethoxytrityl)-2'-desoxythymidine (2c), a solution of 0.60 ml ammonia (33% in water) in 1.92 ml methanol was added to 2b (248 mg, 0.57 mmol) and the mixture was stirred for 2.5 h at RT. Full deprotection of 2b was proved by TLC (hexane/acetone 1:1, R$_f$=0.25). After evaporation of the solvent and coevaporation with methanol (2×4 ml) the resulting yellow solid was dissolved in 3 ml pyridine. After addition of catalytic amounts of DMAP the mixture was cooled down to 0° C. A suspension of 4,4'-dimethoxytritylchloride (380 mg, 1.15 mmol) in pyridine was added and the reaction mixture was stirred for 18 h at RT. Then 2 ml ethanol was added and the solvents were evaporated. Purification was done by flash chromatography (hexane/acetone 2:1, 1% TEA→hexane/acetone 1:1, 1% TEA) yielded 2c (275 mg, 0.42 mmol, 74%) as a white foam.

$^1$H-NMR (500 MHz, CDCl$_3$, 25° C., TMS): δ=0.60-0.63 (m, 1H$_{endo}$), 1.14-1.35 (m, 6H$_{exo/endo}$), 1.45 (ddd, $^2$J=8.23 Hz, $^3$J=4.10 Hz, 2.02 Hz, 1H$_{endo}$), 1.58 (d, $^4$J=1.00 Hz, 6H$_{exo/endo}$), 1.85 (ddd, $^2$J=11.76 Hz, $^3$J=9.31 Hz, 3.86 Hz, 1H$_{endo}$), 2.23-2.29 (m, 2H$_{exo/endo}$), 2.49-2.55 (m, 1H$_{endo}$), 2.60 (ddd, $^2$J=13.59 Hz, $^3$J=6.14 Hz, 3.99 Hz, 2H$_{exo/endo}$), 2.75-2.92 (m, 4H$_{exo/endo}$), 3.37 (dd, $^2$J=10.55 Hz, $^3$J=3.31 Hz, 2H$_{exo/endo}$), 3.46-3.50 (m, 2H$_{exo/endo}$), 3.79 (s, 12H$_{exo/endo}$), 3.92 (ddd, $^2$J=10.91 Hz, $^3$J=9.58 Hz, $^4$J=1.42 Hz, 1H$_{endo}$), 4.06-4.09 (m, 1H$_{endo}$), 4.18 (dd, $^3$J=10.92 Hz, 6.75 Hz, 2H$_{exo/endo}$), 4.25 (ddd, $^2$J=11.04 Hz, $^3$J=9.19 Hz, J=4.78 Hz, 1H$_{exo}$), 4.44-4.48 (m, 1H$_{exo}$), 4.50-4.55 (m, 2H$_{exo/endo}$), 5.91-5.94 (m, 1H$_{endo}$), 6.08-6.11 (m, 2H$_{exo}$), 6.14-6.16 (m, 1H$_{endo}$) 6.37-6.40 (m, 2H$_{exo/endo}$), 6.82-6.85 (m, 8H$_{exo/endo}$), 7.21-7.30 (m, 14H$_{exo/endo}$), 7.38-7.41 (m, 4H$_{exo/endo}$), 7.81 (dd, $^4$J=2.66 Hz, 1.00 Hz, 1H$_{endo}$), 7.82 (d, $^4$J=1.00 Hz, 1H$_{exo}$). $^{13}$C NMR (75 MHz, CDCl$_3$, 25° C., TMS): δ=11.8, 31.3, 37.6, 41.4, 41.6, 41.9, 42.2, 43.6, 43.8, 49.1, 49.3, 55.2, 63.2, 70.7, 71.4, 72.0, 85.9, 86.2, 86.8, 104.8, 113.2, 127.0, 128.0, 128.1, 130.0, 132.1, 135.5, 137.0, 137.5, 137.6, 139.2, 144.4, 156.0, 158.6, 170.4. MS (EI$^+$): m/z 650.1 (calculated for [C$_{39}$H$_{42}$N$_2$O$_7$]$^{-+}$ 650.3).

O$^4$-(Bicyclo[2.2.1]hept-2-en-2-ylmethyl)-5'-O-(4,4'-dimethoxytrityl)-2'-desoxythymidine-3'-O-[O-(2-cyanoethyl)-N,N'-diisopropylphosphoramidite] (2) was synthesized from 2c following the same synthetic procedure as for 1. Purification by flash chromatography (hexane/acetone 3:2, 1% TEA) afforded the clean product as colourless oil (245 mg, 0.29 mmol, 76%) in an exo/endo ratio of 1:4.

$^{13}$C-NMR (75 MHz, CDCl$_3$, 25° C., TMS): δ=11.5, 20.2, 24.5, 28.8, 29.5, 37.6, 41.0, 42.2, 43.1, 43.2, 43.3, 43.6, 43.9, 46.2, 49.3, 55.2, 58.4, 63.0, 70.7, 73.5, 85.3, 86.2, 86.7, 104.9, 113.2, 117.4, 127.1, 127.9, 128.2, 130.2, 132.2, 135.4, 137.0, 137.5, 139.3, 144.3, 156.0, 158.7, 170.4. $^{31}$P-NMR (121 MHz, CDCl$_3$, 25° C., H$_3$PO$_4$): δ=148.7 (d, J=148.7 Hz). MS (FAB$^+$): m/z 851.1 (calculated for [(C$_{48}$H$_{59}$N$_4$O$_8$P$_1$)+H]$^+$ 851.4).

Example 4

Synthesis of (Aminopropyl)-CPG-mono-O-(4,4'-dimethoxytrityl)-cis-endo-2,3-bis(hydroxy-methyl)bicyclo[2.2.1]hept-5-ene (4)

Compound 4a was synthesized according to published procedures (M. Zhang, D. L. Flynn, P. R. Hanson, *J. Org. Chem.* 2007, 72, 3194-3198)

Figure 6:
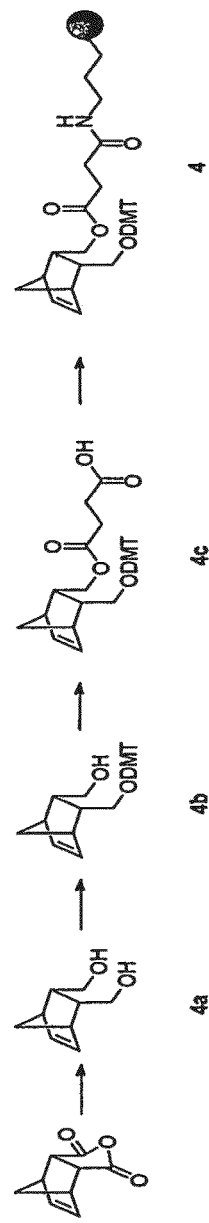
FIG. 6 shows reaction Scheme to prepare Compound 4

The synthesis scheme is shown in FIG. 6.

To prepare Mono-O-(4,4'-dimethoxytrityl)-cis-endo-2,3-bis(hydroxymethyl)bicyclo[2.2.1]hept-5-ene (4b), 4,4'-dimethoxytritylchloride (1.21 g, 3.58 mmol, 0.9 eq) was added to a solution of 4a (621 mg, 4.03 mmol) in 10 ml pyridine and the solution was stirred for 15 h at RT. After evaporation of the solvent the residue was dissolved in CH$_2$Cl$_2$ and extracted with NaHCO$_3$-solution and water. Drying over Na$_2$SO$_4$ and removal of the solvent under reduced pressure afforded the crude product. Purification by flash chromatogtaphy (CHCl$_3$, 1% TEA) gave 4c (775 mg, 1.70 mmol, 42%) as a yellow oil.

$^1$H-NMR (500 MHz, CDCl$_3$, 25° C., TMS): δ=1.38-1.40 (m, 2H), 2.54-2.59 (m, 1H), 2.63 (t, $^2$J=9.55 Hz, 1H), 2.71-2.77 (m, 1H), 2.79-2.80 (m, 2H), 3.03-3.07 (m, 1H), 3.22 (dd, $^2$J=9.55 Hz, $^3$J=4.55 Hz, 1H), 3.25-3.30 (m, 1H), 3.41 (m, 1H), 3.77-3.79 (m, 6H), 5.75 (dd, $^3$J=5.72 Hz, 2.93 Hz, 1H), 5.89 (dd, $^3$J=5.72 Hz, 2.93 Hz, 1H), 6.82-6.85 (m, 4H), 7.18-7.35 (m, 7H), 7.42-7.44 (m, 2H). $^{13}$C-NMR (75 MHz, CDCl$_3$, 25° C., TMS): δ=42.1, 45.5, 46.4, 46.6, 49.7, 55.1, 63.0, 64.6, 86.8, 113.1, 126.7, 127.7, 127.9, 129.1, 129.6, 129.8, 134.4, 134.8, 135.5, 136.1, 144.6, 158.4. MS (EI$^+$): m/z 456.3 (calculated for [(C$_{30}$H$_{32}$O$_4$)]$^{-+}$ 456.3).

To prepare O-(4-Oxo-butanoic acid)-O-(4,4'-dimethoxytrityl)-cis-endo-2,3-bis(hydroxymethyl)bicycle[2.2.1]hept-5-ene (4c), 4b (775 mg, 1.70 mmol) was dissolved in 17.5 ml pyridine before addition of succinic anhydride (170 mg, 1.70 mmol) and DMAP (104 mg, 0.85 mmol). The reaction mixture was then stirred for 17 h at RT. After evaporation of the solvent and co-distillation with toluene (3×10 ml) the obtained residue was dissolved in 50 ml CH$_2$Cl$_2$ and extracted with NaHCO$_3$-solution and water. Drying over Na$_2$SO$_4$ and removal of the solvent yielded 4c (514 mg, 0.92 mmol, 54%) as a white foam.

$^1$H-NMR (500 MHz, CDCl$_3$, 25° C., TMS): δ=1.31 (d, $^2$J=8.20 Hz, 1H), 1.46 (td, $^2$J=8.20 Hz, $^3$J=1.68 Hz, 1H), 2.40-2.63 (m, 7H), 2.82-2.84 (m, 1H), 2.89 (dd, $^2$J=8.39 Hz, $^3$J=5.31 Hz, 1H), 3.08-3.12 (m, 1H), 3.43 (dd, J=10.67 Hz, 9.93 Hz, 1H), 3.75-3.80 (m, 7H), 5.85 (dd, $^3$J=5.75 Hz, 2.85 Hz, 1H), 5.97 (dd, $^3$J=5.74 Hz, 2.85 Hz, 1H), 6.80-6.84 (m, 4H), 7.17-7.31 (m, 7H), 7.41-7.43 (m, 2H). $^{13}$C-NMR (75 MHz, CDCl$_3$, 25° C., TMS): δ=29.7, 29.9, 40.4, 42.0, 45.3, 45.7, 48.8, 55.2, 62.7, 64.9, 85.6, 113.0, 126.6, 127.7, 128.2, 129.1, 130.0, 135.0, 135.7, 136.4, 136.5, 145.2, 158.3, 172.5, 176.2). MS (FAB$^+$): m/z 556.1 (calculated for [C$_{34}$H$_{36}$O$_7$]$^+$ 851.4).

To prepare (Aminopropyl)-CPG-mono-O-(4,4'-dimethoxytrityl)-cis-endo-2,3-bis(hydroxy-methyl)bicyclo[2.2.1]hept-5-ene (4), p-nitrophenole (35.0 mg, 0.25 mmol) and N,N'-dicyclohexylcarbodiimide (144 mg, 0.70 mmol) was added to a solution of 4c (171 mg, 0.25 mmol) in 4 ml dioxane and 0.2 ml pyridine and the mixture was stirred at RT for 15 h. Precipitated urea was filtered and the filtrate (2 ml) was added to OH-capped CPG suspended in 1 ml DMF. After standing for 72 h at RT CPG was filtered and the resin washed with methanol and diethylether. For blocking unreacted aminogroups, 20 μl acetic anhydride, 40 μl pyridine and 1 mg DMAP were added to the CPG. After 30 min at RT the resin was filtered and washed with methanol and diethylether. For calculating norbornene-loading CPG 4 was treated with 2% dichloroacetic acid in $CH_2Cl_2$. After measuring absorbance at 505 nm a loading of 23 μmol 4c per gram of CPG was determined using following equation:

$$\text{Loading} = \frac{\text{Volume [ml]} \times \text{Absorbance (505 nm)} \times 1000}{\varepsilon \text{ [ml/(cm} \times \mu\text{mol)]} \times \text{Mass [mg]}}$$

Synthesis of Compound 8

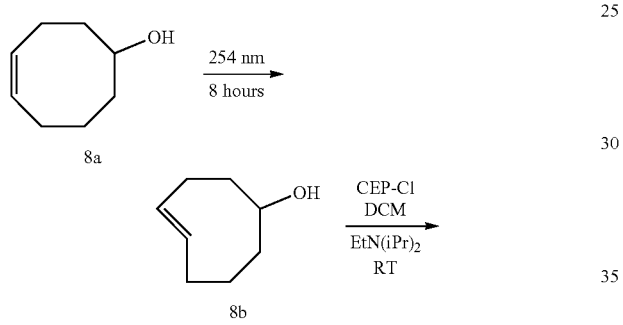

(E)-Cyclooct-4-enol (8b): (E)-cyclooct-4-enol was synthesized from (Z)-cyclooct-4-enol (H. Meier, W. Mayer, H. Kolshorn, *Chem. Ber.* 1987, 120, 685-689) by modification of previously published procedures (M. Royzen, G. P. A. Yap, J. M. Fox, *J. Am. Chem. Soc.* 2008, 130, 3760-3761; N. K. Devaraj, R. Upadhyay, J. B. Haun, S. A. Hilderbrand, R. Weissleder, *Angew. Chem.* 2009, 48, 7013-7016). 2 g (15.9 mmol) (Z)-cyclooct-4-enol and 2.2 g (16.3 mmol) methyl benzoate were dissolved in 250 mL cyclohexane/diethyl ether=1:9. The Petri dish was placed in an UVP-CL-1000-ultraviolet crosslinker reactor and irradiated for eight hours under ice-cooling. In intervals of 25-30 minutes the reaction mixture was passed through a column packed with 27 g of silver nitrate (10%) impregnated silica (commercially available from Aldrich). The mixture passing through the column was placed back into the UV crosslinker for further irradiation. After eight hours the irradiation was stopped and the silica was added to an ammonium hydroxide solution (28%, 160 ml). The suspension was stirred for 5 minutes, 160 ml of diethylether were added and stirring continued for 5 minutes. The aqueous layer was extracted with ether, the combined organic phases were washed with water and dried over magnesium sulfate. After evaporation of the solvents and flash chromatography (cyclohexane/ethyl acetate=1:1) two separated diastereomers of the product could be isolated. The main product 8b was obtained as a colourless oil (455 mg, 3.61 mmol, 23%) and used for further steps.

$^1$H NMR (500 MHz, $CDCl_3$, 25° C., TMS): δ=1.38 (m, 1H, OH), 1.48-1.74 (m, 3H), 1.88-2.00 (m, 4H), 2.23-2.38 (m, 3H), 3.43-3.48 (m, 1H), 5.34-5.42 (m, 1H), 5.54-5.61 (m, 1H). $^{13}$C {$^1$H} NMR (500 MHz, $CDCl_3$): δ=31.2 31.2, 32.6, 34.3, 44.1, 44.6, 77.7, 132.8, 135.1.

(E)-2-Cyanoethyl cyclooct-4-enyl diisopropylphosphoramidite (8): To a solution of (E)-Cyclooct-4-enol (70 mg, 0.56 mmol) in 2 ml of absolute $CH_2Cl_2$ under argon diisopropylethylamine (0.33 ml, 1.90 mmol) was added. The mixture was cooled to 0° C. and 2-cyanoethyl-N,N-diisopropylchlorophosphoramidite (141 μl, 0.63 mmol, 1.05 eq) was added. After stirring for one hour at RT, the reaction mixture was directly loaded on a silica column. Purification by flash chromatography (hexane/ethyl acetate 95:5) yielded the product as colourless oil (100 mg, 0.31 mmol, 55%).

$^1$H-NMR (500 MHz, $CDCl_3$, 25° C., TMS): δ=1.16-1.19 (m, 12H), 1.55-1.63 (m, 2H), 1.86-2.37 (m, 8H), 2.63 (t, J=6.55 Hz, 2H), 3.51-3.61 (m, 3H), 3.72-3.85 (m, 2H), 5.38-5.44 (m, 1H), 5.54-5.61 (m, 1H). $^{13}$C {$^1$H, $^{31}$P} NMR (75 MHz, $CDCl_3$, 25° C., TMS): δ=20.3, 24.4, 24.6, 31.1, 31.3, 32.7, 32.8, 34.4, 40.0, 40.3, 42.9, 43.0, 43.2, 58.1, 58.3, 79.6, 80.0, 117.6, 132.6, 135.1, 135.2. $^{31}$P-NMR (121 MHz, $CDCl_3$, 25° C., $H_3PO_4$): δ=145.5, 146.0.

Synthesis of Compound 9

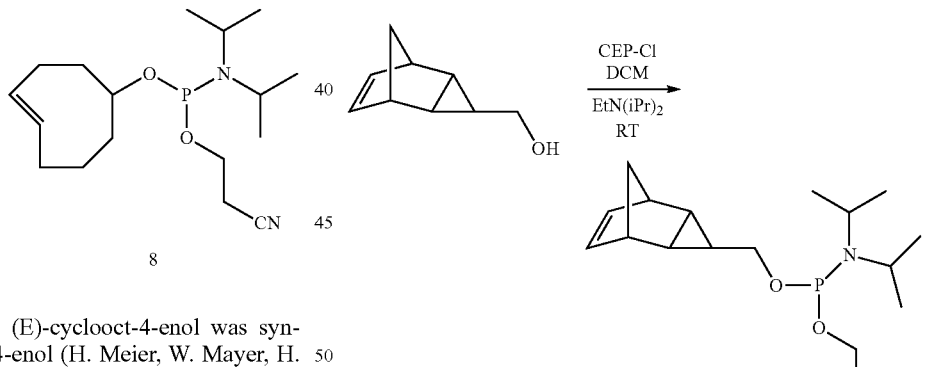

Tricyclo[3.2.1.02.4]oct-6-ene-3-ylmethyl 3-cyanoethyl-diisopropylphosphoramidite (9): To a solution of Tricyclo [3.2.1.02.4]oct-6-ene-3-methanol (158 mg, 1.16 mmol) in 3 ml of absolute $CH_2Cl_2$ diisopropylethylamine (0.33 ml, 1.90 mmol) was added under argon atmosphere. The mixture was cooled to 0° C. and 2-cyanoethyl-N,N-diisopropylchlorophosphoramidite (640 μl, 1.22 mmol, 1.05 eq) was added. After stirring for one hour at RT, TLC showed full conversion and the reaction mixture was directly loaded on a silica column. Purification by flash chromatography (hexane/ethyl acetate 95:5, 5% TEA) yielded the product as colourless oil (350 mg, 104 mmol, 90%).

$^{31}$P-NMR (121 MHz, CDCl$_3$, 25° C., H$_3$PO$_4$): δ=148.1, 148.7. MS (FAB$^+$): m/z 337.3 (calculated for [C$_{18}$H$_{29}$N$_2$O$_2$P$_1$+H]$^+$ 337.2).

Synthesis of Compound 10

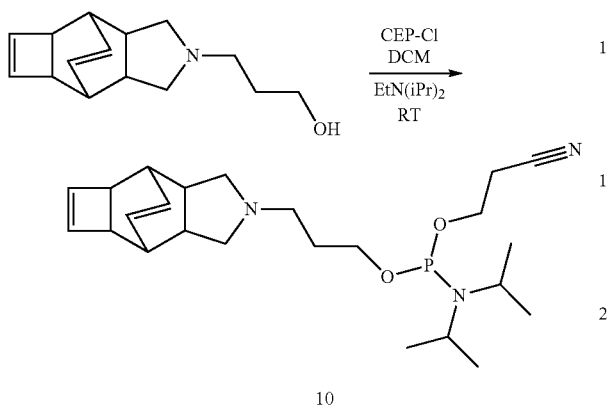

10

4,7-Etheno-1H-cyclobut[f]isoindole, 2,3,3a,4,4a,6a,7,7a-octahydropropyl 3-cyanoethyl-diisopropylphosphoramidite (10): To a solution of 7-Etheno-1H-cyclobut[f]isoindole, 2,3,3a,4,4a,6a,7,7a-octahydropropyl 3-ol (50 mg, 216 μmol) in 1 ml of acid-free CH$_2$Cl$_2$ under argon, diisopropylethylamine (0.33 ml, 0.69 mmol) was added. The mixture was cooled to 0° C. and 2-cyanoethyl-N,N-diisopropylchlorophosphoramidite (53.6 mg, 227 μmol, 1.05 eq) was added. After stirring for 2 h at RT the reaction mixture was directly loaded on a silica column. Purification by flash chromatography (hexane/ethyl acetate 1:1, 2% TEA) afforded the clean product as colourless oil (90 mg, 209 μmol, 97%).

$^1$H-NMR (500 MHz, CDCl$_3$, 25° C., TMS): δ=1.17 (t, J=6.43 Hz, 12H), 1.76-1.82 (m, 2H), 1.97-2.00 (m, 2H), 2.38-2.50 (m, 4H), 2.47-2.57 (m, 2H), 2.63 (t, J=6.55 Hz, 2H), 2.70-2.71 (m, 2H), 3.03-3.10 (m, 2H), 3.54-3.72 (m, 4H), 3.76-3.88 (m, 2H), 5.87 (s, 2H), 5.89 (dd, J=3.44, 4.57 Hz, 2H). $^{13}$C {$^1$H,} NMR (75 MHz, CDCl$_3$, 25° C., TMS): δ=20.0, 22.2, 29.4, 37.6, 43.4, 45.6, 45.9, 51.9, 59.3, 59.7, 64.8, 116.3, 130.3, 137.9. $^{31}$P-NMR (121 MHz, CDCl$_3$, 25° C., H$_3$PO$_4$): δ=147.5. MS (FAB$^+$): m/z 432.4 (calculated for [C$_{24}$H$_{38}$N$_3$O$_2$P$_1$+H]$^+$ 432.3).

Example 5

Oligonucleotide Synthesis

Oligonucleotide synthesis was performed at 1 μmol scale in the DMT-ON mode using standard reagents and standard protocols for DNA. All oligonucleotides were purified by semi-preparative HPLC, de-tritylated in a 2% aqueous trifluoroacetic acid solution, neutralized and isopropanol precipitated. The purity of the oligonucleotides was analysed by reversed-phase HPLC and MALDI-TOF mass spectrometry (Table 1).

TABLE S1

Synthesized oligonucleotides, HPLC and MALDI-TOF analysis.

| ODN[c] | Sequence[a] | Retention time [min] | [M + H]$^+$ calculated | [M + H]$^+$ observed |
|---|---|---|---|---|
| ODN1a | 5'-WTGCTCA-3' | 26.0 | 1953.4 | 1954.1[b] |
| ODN1b | 5'-TGCXTCA-3' | 28.6 | 2177.5 | 2177.7 |
| ODN1c | 5'-TGCTCAZ-3' | 21.8 | 1999.4 | 2000.1 |
| ODN2a | 5'-WGGAGCTCAGCCTTCACTGC-3' | 22.9 | 5952.9 | 5947.4[b] |
| ODN2b | 5'-GGAGCXCAGCCTTCACTGC-3' | 26.2 | 5871.9 | 5870.0[b] |
| ODN2c | 5'-GGAGCYCAGCCTTCACTGC-3' | 26.8 | 5940.0 | 5941.4[b] |
| ODN2e | 5'-WGTGGATCCGACCGTGGTGCC-3' | 23.6 | 6336.1 | 6335.9[b] |
| ODN2f | 5'-WGGAGCTCAGCCTTCACYGC-3' | 30.3 | 6126.1 | 6127.0[b] |
| ODN2g | 5'-W$_1$GGAGCTCAGCCTTCACTGC-3' | 24.0 | 5951.0 | 5951.3[b] |
| ODN2h | 5'-W$_2$GGAGCTCAGCCTTCACTGC-3' | 23.2 | 5961.0 | 5960.6[b] |
| ODN2i | 5'-W$_3$GGAGCTCAGCCTTCACTGC-3' | 22.3 | 6056.1 | 6055.9[b] |
| ODN3a | 5'-GGAGCTCAGCCTTCACTGC-3' | 23.0 | 5765.8 | 5766.9[b] |
| ODN3b | 5'-GTGGATCCGACCGTGGTGCC-3' | 19.4 | 6150.0 | 6149.2[b] |

[a]W = Modification based on phosphoramidite 1, W$_1$ = Modification based on Phosphoramidite 8, W$_2$ = Modification based on Phosphoramidite 9, W$_3$ = Modification based on Phosphoramidite 10, X = DNA nucleotide based on 2, Y = DNA nucleotide based on 3, Z = Modification based on 4.
[b]purified by Zip tip. DHPLC-chromatograms of the purified oligonucleotides are shown in FIG. 7.
[c]ODN1a = SEQ ID NO: 1, ODN1b = SEQ ID NO: 2, ODN1c = SEQ ID NO: 3, ODN2a = SEQ ID NO: 4, ODN2b = SEQ ID NO: 5, ODN2c = SEQ ID NO: 6, ODN2e = SEQ ID NO: 8, ODN2f = SEQ ID NO: 9, ODN2g = SEQ ID NO: 16, ODN2h = SEQ ID NO: 17, ODN2i = SEQ ID NO: 18, ODN3a = SEQ ID NO: 10, ODN3b = SEQ ID NO: 11

Example 6

Inverse Diels-Alder Reactions of Small Oligonucleotides

General Procedure:

All reactions were carried out in aqueous solution (pH≤7) at RT and analysed by HPLC and MALDI-TOF mass spectrometry (Table S2). Concentrations of tetrazine stock solutions were determined by measuring absorbance and calculating concentrations by Lambert-Beer's law ($\epsilon(290\ nm)=33000\ l\ (mol\cdot cm)^{-1}$). Concentrations of oligonucleotide stock solutions were determined by measuring absorbance via Nanodrop ND-1000 spectrophotometer. For performing inverse DA reactions stock solutions of diene and dienophile were mixed and reacted for different periods of time at RT.

HPLC and MALDI-TOF Analysis:

For HPLC analysis reaction mixtures were loaded on the column without further purification and analysed using different gradients. Fractions containing the Diels-Alder product were collected, lyophilized and in case of ODN1b and ODN2a-f desalted via Zip tip$_{C18}$ before submitting for MALDI-TOF mass spectrometry (FIG. 9).

TABLE S2

Performed Diels-Alder reactions, HPLC and MALDI-TOF analysis.

| Dienophile | Diene | Retention time [min] | [M + H]+ calculated | [M + H]+ observed |
|---|---|---|---|---|
| ODN1a | 5 | 20.8-26.5 | 2205.4 | 2205.1 |
| ODN1a | 6 | 35.4-37.5 | 2480.2 | 2481.1 |
| ODN1b | 5 | 20.8-24.6 | 2428.5 | 2429.8[a] |
| ODN1c | 5 | 41.6-42.7[b] | 2251.5 | 2251.2 |
| ODN2a | 5 | 20.1-29.4 | 6204.9 | 6202.8[a] |
| ODN2a | 6 | 19.8-27.5 | 6478.7 | 6479.6[a] |
| ODN2b | 5 | 31.3-39.1 | 6123.9 | 6123.2[a] |
| ODN2c | 5 | 27.4-34.4 | 6192.9 | 6189.5[a] |
| ODN2d | 5 | 27.4-34.4 | 6192.9 | 6193.3[a] |
| ODN2d | 6 | 19.8-25.3 | 6466.7 | 6467.9[a] |
| ODN2f | 6 | — | 6652.8/7180.0 | 6648.8/7174.0 |

[a]Purified and desalted by Zip tip$_{C18}$.
[b]DMT-ON product.

Due to the isomeric variety of the Diels-Alder product there was always more than one product peak appeared in the HPLC-chromatogram. FIG. 8 is showing HPLC-chromatograms of performed Diels-Alder reactions between 5' modified hexamer ODN1a (left up) or rather internally modified 19mer ODN2c (right up) and diene 5. As negative control unmodified oligonucleotides were added to 5 and after standing at RT for 24 h (hexamer, left down) or rather 60 h (19mer ODN3a, right down) unreacted oligonucleotides were determined by HPLC.

To analyze the temperature dependence of the inverse DA reaction dienophile ODN1a was reacted with tetrazine 5 (ratio 1:1) for four hours at RT and at 80° C. Recorded HPLC-chromatograms (FIG. 10) are indicating different peak patterns at different reaction temperatures. Corresponding to the known endo-rule there is more exo-product ($t_R$=24.4-24.7 min) formed at 80° C.

Example 7

Synthesis of 109mer Oligonucleotides

Modified primers ODN2a-d were incorporated into a long double-stranded DNA via PCR reaction using a 109mer double-stranded DNA pool as template having 70 randomized positions and constant regions for reverse and forward primers. For PCR reaction standard protocols were followed using Taq polymerase, 62° C. as annealing temperature and performing 6 cycles. PCR yielded a clean product for all primers either non-, internally and/or 5'-modified. For removing primers, the PCR product was purified using a commercial PCR purification kit.

Sequences:

Reverse primer:
(SEQ ID NO: 12)
5'-GTG GAT CCG ACC GTG GTG CC-3'

Forward primer:
(SEQ ID NO: 13)
5'-GGA GCT CAG CCT TCA CTG C-3'

Pool
(SEQ ID NO: 14)
5'GGAGCTCAGCCTTCACTGC-N70-GGCACCACGGTCGGATCCAC-3'

(SEQ ID NO: 15)
3'CCTCGAGTCGGAAGTGACG-N70-CCGTGGTGCCAGCCTAGGTG-5'

Example 8

Gel Analysis for Inverse DA Reaction of 109mer (1) dsPCR Product Carrying One Dienophile For inverse DA reaction 10 eq of biotin tetrazine 7 were added to the 5'-modified 109mer PCR product (c=3.47 μM in water) and incubated at RT. Aliquots were withdrawn after 0 min, 10 min, 20 min, 30 min, 60 min, 90 min, 120 min and 150 min. To quench the reaction six volumes of TRIS-buffer (pH=8.5) were added to each aliquot and aliquots then stored at −80° C. Before loading onto a 2% agarose gel 1 eq of streptavidin was added to each sample and the gel run for 40 min at 200 V (FIG. 11)

(2) dsPCR Products Carrying More than One Dienophile 10 eq of biotin-tetrazine 7 per dienophilic modification were added to the modified PCR products (c=1.52 μM in water) and incubated at RT for 15 h. Before loading onto a 2% agarose gel 1 eq of streptavidin was added and the gel run for 15 min at 170 V (FIG. 11).

Melting curve measurements were carried out in HEPES buffer (15 mM), containing 150 mM $NaClO_4$ and 7.5 mM $Mg(ClO_4)_2$. The results are shown in FIG. 12.

Example 9

Gel Analysis for Inverse DA Reaction of 109mer

To extend the application, ODN2f (carrying two dienophiles) was synthesized. An inverse Diels-Alder reaction was carried out with tetrazine 6 under the same condition as described in Example 6, and analysis by MALDI-TOF mass spectroscopy confirmed the formation of single and double Diels Alder product. Finally, a double-stranded DNA (109 mer) was amplified by PCR with ODN 2a, c, e-f as forward and reverse primers carrying either one or two dienophiles. After overnight inverse Diels-Alder reaction with 10-fold excess of tetrazine 7 per dienophile modification, a 2% agarose gel (stained with ethidum bromide) was made (FIG. 13). Conversions up to >95% for the double DA product (FIG. 13, lanes 4-5) and 75% for triple DNA product (FIG. 13, lane 6) could be obtained.

The invention claimed is:

1. A method for the post-synthetic modification of nucleic acids, comprising the following steps:
   (a) preparing trans-cyclooctene-modified oligonucleotides,
   (b) preparing modified tetrazines, and
   (c) reacting the trans-cyclooctene-modified oligonucleotides with the modified tetrazines via inverse Diels Alder reaction.

2. The method of claim 1, wherein the tetrazines are modified with a compound selected from the group consisting of fluorescent, luminescent or phosphorescent dyes, and affinity tags.

3. The method of claim 1, wherein the oligonucleotide is singly or multiply modified.

4. The method of claim 3, wherein the oligonucleotide is modified terminally and/or internally.

5. The method of claim 4, wherein the terminal modification is 3' and/or 5'.

6. The method of claim 1, wherein the oligonucleotide has a length between 3 and 500 nucleotides.

7. The method of claim 1, wherein the oligonucleotide is single-stranded or double-stranded DNA or RNA, a nucleic acid analog or chimera thereof with DNA and/or RNA or an enzymatically modified PCR product.

8. The method of claim 1, wherein the trans-cyclooctene-modified oligonucleotide is prepared by reacting an oligonucleotide with the following compound:

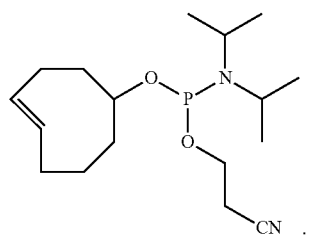

9. The method of claim 1, wherein the tetrazine is selected from the following compounds:

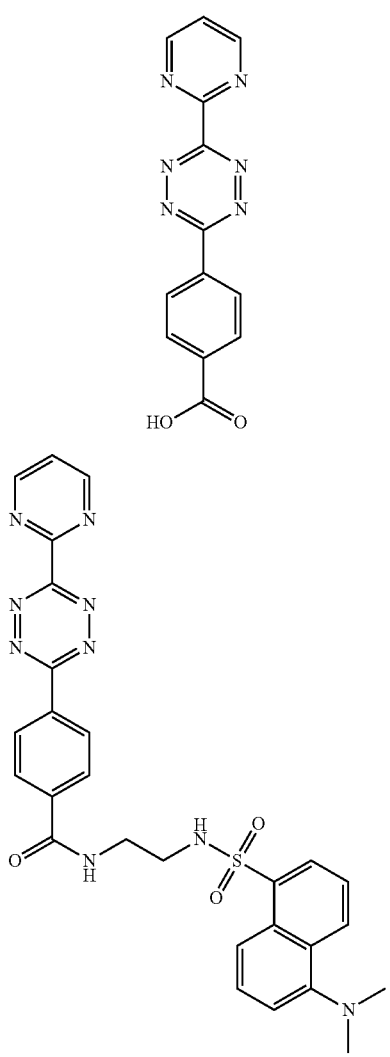

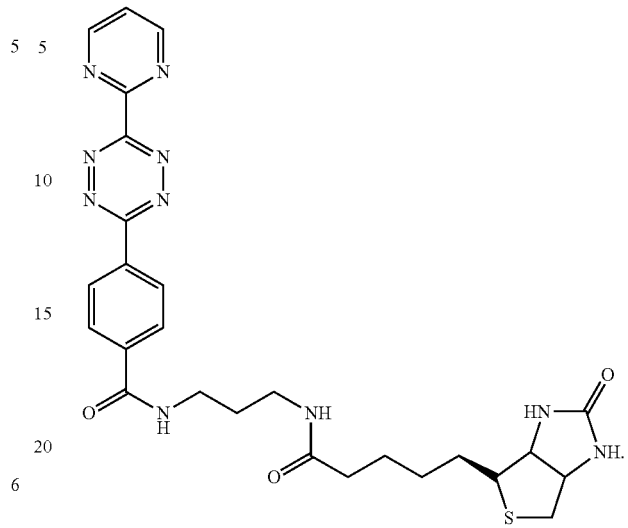

10. The method of claim 1, wherein the inverse Diels Alder reaction between the modified oligonucleotide and the modified tetrazine uses equimolar amounts of both components if the oligonucleotide is below 100 nucleotides.

11. The method of claim 1, wherein the inverse Diels Alder reaction between the modified oligonucleotide and the modified tetrazine uses the tetrazine in 2-20-fold excess if the oligonucleotide is larger than 100 nucleotides.

12. The method of claim 10, wherein the inverse Diels Alder reaction takes place between 0 and 100° C. in aqueous media.

13. The method of claim 10, wherein modified oligonucleotides in concentrations of at least 500 μM are reacted.

* * * * *